United States Patent
Varshney

(10) Patent No.: US 10,854,326 B2
(45) Date of Patent: Dec. 1, 2020

(54) SYSTEMS AND METHODS FOR FULL BODY CIRCULATION AND DRUG CONCENTRATION PREDICTION

(71) Applicant: VERISIM LIFE INC., San Francisco, CA (US)

(72) Inventor: Jyotika Varshney, San Francisco, CA (US)

(73) Assignee: VERISIM LIFE INC., San Francisco, CA (US)

(*) Notice: Subject to any disclaimer, the term of this patent is extended or adjusted under 35 U.S.C. 154(b) by 0 days.

(21) Appl. No.: 16/197,260

(22) Filed: Nov. 20, 2018

(65) Prior Publication Data

US 2019/0156933 A1     May 23, 2019

Related U.S. Application Data

(60) Provisional application No. 62/589,466, filed on Nov. 21, 2017.

(51) Int. Cl.
| | | |
|---|---|---|
| *G16H 20/17* | (2018.01) | |
| *A61M 5/168* | (2006.01) | |
| *G06N 20/00* | (2019.01) | |
| *G16H 50/50* | (2018.01) | |
| *A61M 5/142* | (2006.01) | |

(52) U.S. Cl.
CPC ............ *G16H 20/17* (2018.01); *A61M 5/168* (2013.01); *A61M 2005/14208* (2013.01); *A61M 2205/505* (2013.01); *G06N 20/00* (2019.01); *G16H 50/50* (2018.01)

(58) Field of Classification Search
None
See application file for complete search history.

(56) References Cited

U.S. PATENT DOCUMENTS

| | | | |
|---|---|---|---|
| 6,542,858 B1 * | 4/2003 | Grass | G16C 20/60 703/2 |
| 6,647,358 B2 * | 11/2003 | Grass | G16C 20/60 703/2 |

(Continued)

FOREIGN PATENT DOCUMENTS

KR    101298303    8/2013

OTHER PUBLICATIONS

Zhuang, X. et al.; "PBPK modeling and simulation in drug research and development" (Review); Acta Pharmaceutica Sinica B 2016; 6(5):430-440. (Year: 2016).*

(Continued)

*Primary Examiner* — Karlheinz R. Skowronek
*Assistant Examiner* — Marie Archer
(74) *Attorney, Agent, or Firm* — Foley & Lardner LLP

(57) ABSTRACT

A method for predicting drug concentration levels includes receiving at least one subject characteristic of the subject, and executing a full body circulation model by: determining a first concentration of the drug in a first blood flow entering a first organ determining a second concentration of the drug in the first organ, determining a third concentration of a drug in a third blood flow entering a second organ, the third blood flow downstream of the first organ, and determining, using the second organ model a fourth concentration of the drug in the second organ.

16 Claims, 15 Drawing Sheets

(56) References Cited

U.S. PATENT DOCUMENTS

| | | | | |
|---|---|---|---|---|
| 8,589,175 | B2* | 11/2013 | Glauser | G06Q 50/24 |
| | | | | 705/2 |
| 9,153,024 | B2* | 10/2015 | Ananda Yogendran | |
| | | | | G06T 7/0016 |
| 2004/0133581 | A1* | 7/2004 | Shinjo | G06F 16/258 |
| 2004/0193446 | A1 | 9/2004 | Mayer et al. | |
| 2005/0074803 | A1* | 4/2005 | Schmitt | G16B 20/00 |
| | | | | 435/6.16 |
| 2008/0033661 | A1 | 2/2008 | Syroid et al. | |
| 2009/0028968 | A1* | 1/2009 | Tam | G06K 9/6228 |
| | | | | 424/757 |
| 2009/0171697 | A1 | 7/2009 | Glauser et al. | |
| 2014/0222349 | A1* | 8/2014 | Higgins | G16B 20/00 |
| | | | | 702/19 |
| 2016/0300037 | A1* | 10/2016 | Mould | G16H 20/17 |
| 2016/0335412 | A1* | 11/2016 | Tucker | G06F 19/00 |

OTHER PUBLICATIONS

Kuepfer, L. et al.; "Applied Concepts in PBPK modeling: How to Build a PBPK/PD model"; Pharmacometrics Syst. Pharmacol. (2016) 5, 516-531 (Year: 2016).*

Lipscomb J.C. et al; (2012) Physiologically-Based Pharmacokinetic (PBPK) Models in Toxicity Testing and Risk Assessment. In: Balls M., Combes R.D., Bhogal N. (eds) New Technologies for Toxicity Testing. Advances in Experimental Medicine and Biology, vol. 745. Springer, New York, NY; p. 76-95. (Year: 2012).*

Bjorkman S. 2005. Prediction of drug disposition in infants and children by means of physiologically based pharmacokinetic (PBPK) modelling: theophylline and midazolam as model drugs. Br. J. Clin. Pharmacol. 59:691-704. (Year: 2005).*

Maharaj, A.R. et al; "Physiologically Based Pharmacokinetic Modeling and Simulation in Pediatric Drug Development"; CPT Pharmacometrics Syst. Pharmacol. (2014) 3, e148. (Year: 2014).*

Barrett, J.S. et al; "Physiologically Based Phrmacokinetic (PBPK) Modeling in Children"; Clinical Pharmacology Therapeutics: vol. 92; No. 1; Jul. 2012; p. 40-49. (Year: 2012).*

Reddy, M. B. et al; (Jan. 23, 2013). "Physiologically Based Pharmacokinetic Modeling: A Tool for Understanding ADMET Properties and Extrapolating to Human, New Insights into Toxicity and Drug Testing", Sivakumar Gowder, IntechOpen, p. 197-217 (Year: 2013).*

Eissing, T. et al; "A computational systems biology software platform for multiscale modeling and simulation: integrating whole-body physiology, disease biology, and molecular reaction networks"; Frontiers in Physiology; Feb. 2011; vol. 2; Article 4; p. 1-10. (Year: 2011).*

Gillete, J. R.; Sequential Organ First-Pass Effects: Simple Methods for Constructing Compartmental Pharmacokinteic Models from Physiological Models of Drug Disposition by Several Organs; Journal of Pharmaceutical Sciences vol. 71, Issue 6, Jun. 1982, pp. 673-677 (Year: 1982).*

Abbiati, R. A. et al; "A modeling tool for the personalization of pharmacokinetic predictions"; Computers and Chemical Engineering 91 (2016) 28-37 (Year: 2016).*

You, W. et al; (2011) Personalized modeling for drug concentration prediction using Support Vector Machine. In: 4th International conference on biomedical engineering and informatics (BMEI), vol. 3, pp. 1505-1509. (Year: 2011).*

Boyle, J. et al. "Population pharmacokinetics of busulfan in pediatric and young adult patients undergoing hematopoietic cell transplant: a model-based dosing algorithm for personalized therapy and implementation into routine clinical use"; Ther Drug Monit, 37 (2) (2015), pp. 236-245. (Year: 2015).*

Maltarollo, V. G.; et al; (2015) Applying machine learning techniques for ADME-Tox prediction: a review, Expert Opinion on Drug Metabolism & Toxicology, 11:2, 259-271 (Year: 2015).*

Abbiati, R. A.; "A PSE approach to patient-individualized physiologically-based pharmacokinetic modeling"; Computer Aided Chemical Engineering vol. 37, 2015, pp. 77-84. (Year: 2015).*

International Search Report and Written Opinion for International Appl. No. PCT/US2018/062136, dated Mar. 11, 2019.

International Preliminary Report on PCT PCT/US2018/062136 dated Jun. 4, 2020.

* cited by examiner

# SYSTEMS AND METHODS FOR FULL BODY CIRCULATION AND DRUG CONCENTRATION PREDICTION

CROSS-REFERENCE TO RELATED APPLICATIONS

The present disclosure claims the benefit of and priority to U.S. Provisional Application No. 62/589,466, titled "SYSTEMS AND METHODS FOR FULL BODY CIRCULATION AND DRUG CONCENTRATION PREDICTION," filed Nov. 21, 2017, the disclosure of which is incorporated herein by reference in its entirety.

TECHNICAL FIELD

The present disclosure relates generally to drug concentration in organ models, and more particularly to systems and methods for full body circulation and drug concentration prediction, drug toxicity evaluation, and drug dosage amount and delivery method recommendations.

BACKGROUND

Various models are available for estimating drug concentration as a function of time in specific organs, such as the liver. These models typically rely on predetermined parameters for specific drugs, which may not necessarily be accurate representations for specific subjects. In addition, these models typically only model drug metabolism for a single, specific organ. While some models may take into account subject-specific characteristics such as organ volume, age, sex, and weight, it is difficult to create an accurate model which accurately represents the underlying mechanisms of drug metabolism. For example, it can be very difficult to measure a partition coefficient value between the venous blood and the liver for a specific drug, yet it can be crucial to know this value in order to properly model the drug concentration in the liver.

SUMMARY

An aspect of the present disclosure relates to a method for predicting drug concentration levels as a function of time in one or more organs of a subject using a blood flow circulatory system model. The method includes receiving at least one subject characteristic of the subject. The method includes receiving at least one drug characteristic of a drug to be administered to the subject. The method includes executing a full body circulation engine using the at least one subject characteristic to determine a plurality of blood flow rates to the one or more organs of the subject. The method includes determining a first concentration of the drug in a first blood flow entering a first organ based on an initial drug dosage and the blood flow rate to the first organ. The method includes modifying a first drug concentration prediction model of the first organ using the at least one subject characteristic. The method includes determining a second concentration of the drug in the first organ using the modified first drug concentration prediction model. The method includes determining a third concentration of the drug in a second blood flow entering a second organ downstream of the first organ based on the second concentration and the blood flow rate to the second organ. The method includes modifying a second drug concentration prediction model of the second organ using the at least one subject characteristic. The method includes determining a fourth concentration of the drug in the second organ using the modified second drug concentration prediction model.

Another aspect of the present disclosure relates to a system for predicting drug concentration levels as a function of time in one or more organs of a subject using a blood flow circulatory system model. The system includes a subject database including at least one subject characteristic of the subject. The system includes a drug database including at least one drug characteristic of a drug to be administered to the subject. The system includes a drug concentration prediction engine which executes a full body circulation engine using the at least one subject characteristic to determine a plurality of blood flow rates to the one or organs of the subject. The drug concentration prediction engine determines a first concentration of the drug in a first blood flow entering a first organ based on an initial drug dosage and the blood flow rate to the first organ. The drug concentration prediction engine modifies a first drug concentration prediction model of the first organ using the at least one subject characteristic. The drug concentration prediction engine uses the modified first drug concentration prediction model to determine a second concentration of the drug in the first organ. The drug concentration prediction engine determines a third concentration of the drug in a second blood flow entering a second organ downstream of the first organ based on the second concentration and the blood flow rate to the second organ. The drug concentration prediction engine modifies a second drug concentration prediction model of the second organ using the at least one subject characteristic. The drug concentration prediction engine determines a fourth concentration of the drug in the second organ using the modified second drug concentration prediction model.

Another aspect of the present disclosure relates to a method for training a drug concentration prediction model by iteratively adjusting candidate values of missing parameters of the drug concentration prediction model and comparing output generated by the drug concentration prediction model with experimental drug concentration data. The method includes receiving training data including a plurality of subject profiles. Each subject profile includes a known drug concentration and a corresponding at least one subject characteristic. The method includes executing a machine learning engine using the plurality of subject profiles, the machine learning engine including a drug concentration prediction model, to generate predicted drug concentrations. The method includes comparing the predicted drug concentrations to known drug concentrations to generate a comparison result. The method includes determining whether the comparison result satisfies a comparison condition. Responsive to determining that the comparison result does not satisfy the comparison condition, the method includes adjusting at least one parameter of the drug concentration prediction model. Responsive to determining that the comparison result satisfies the comparison condition, the method includes outputting the drug concentration prediction model.

Another aspect of the present disclosure relates to a system for training a drug concentration prediction model by iteratively adjusting candidate values of missing parameters of the drug concentration prediction model and comparing output generated by the drug concentration prediction model with experimental drug concentration data. The system includes a training database storing a plurality of subject profiles. Each subject profile includes a known drug concentration and a corresponding at least one subject characteristic. The system includes a machine learning engine including a plurality of drug concentration prediction models and at least one machine learning engine. The machine learning engine is configured to execute the plurality of drug concentration prediction models to generate a plurality of predicted drug concentrations. The machine learning engine is configured to compare the plurality of predicted drug concentrations to a corresponding plurality of known drug concentrations to generate a comparison result. The machine learning engine is configured to compare the comparison result to a comparison condition. Responsive to the comparison result satisfying the comparison condition, the machine learning engine is configured to output the plurality of drug concentration prediction models. Responsive to the comparison result not satisfying the comparison condition, the machine learning engine is configured to adjust at least one parameter of the drug concentration prediction models.

These and other features and advantages will become apparent from the following detailed description of illustrative embodiments thereof, which is to be read in connection with the accompanying drawings.

Figure 1A:
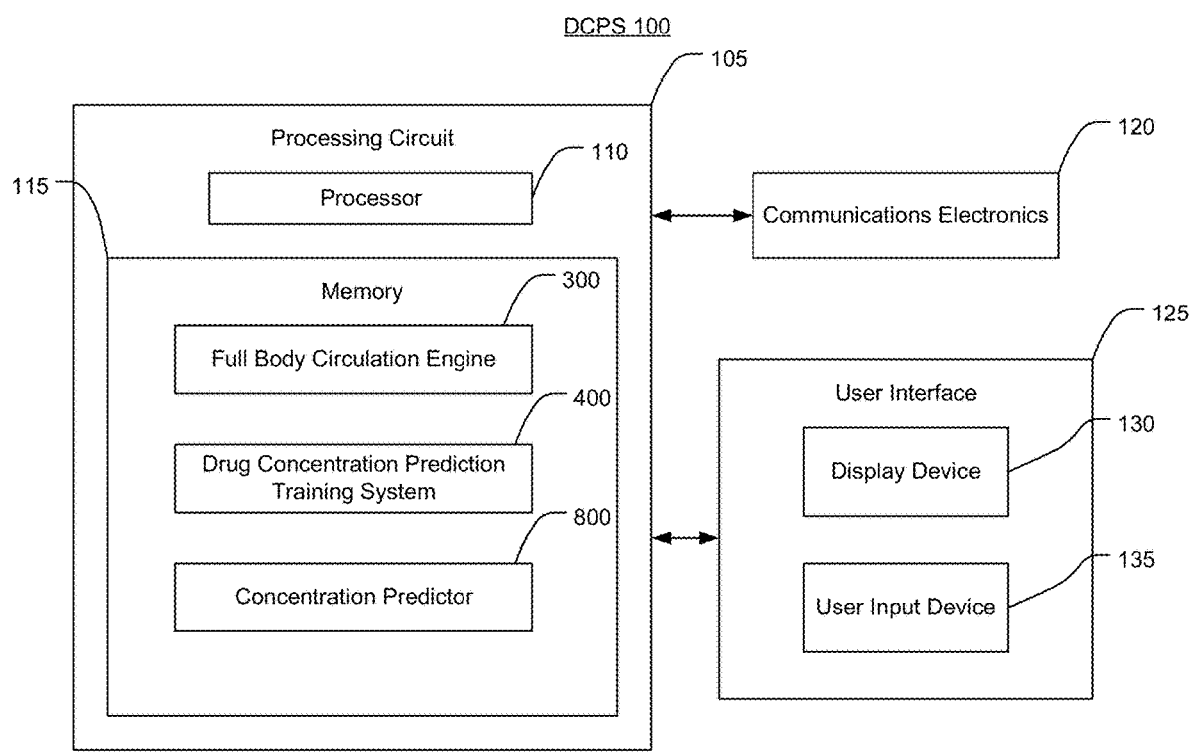
FIG. 1A is a block diagram of a drug concentration prediction system, according to an embodiment of the present disclosure.

It will be recognized that some or all of the figures are schematic representations for purposes of illustration. The figures are provided for the purpose of illustrating one or more embodiments with the explicit understanding that they will not be used to limit the scope or the meaning of the claims.

DETAILED DESCRIPTION

Referring to the Figures generally, systems and methods in accordance with the present disclosure can be used to generate, train, and execute a full body circulation model of blood flow in the human body, including to determine drug concentrations as a function of time in multiple organs and other anatomical systems. Drug concentrations can be determined with greater accuracy and specificity to a subject of interest. Machine learning algorithms can be executed to more accurately model drug absorption, distribution, metabolism, and excretion (ADME), as well as protein behavior, and to uncover previously unknown parameters for modeling the ADME mechanisms. For example, the systems and methods of the present disclosure can extract unknown parameters from experimental data having very little, if any, information about the underlying ADME mechanisms, and can extract parameters for non-linear relationships. Drug dosage and toxicity recommendations can be made, taking into account subject-specific factors such as disease conditions, and to indicate a recommended delivery modality (e.g., oral vs. intravenous). Accuracy can be increased by modifying and/or selecting specific drug concentration prediction models that are more specifically tailored to characteristics of the subject for which the drug concentration information is being predicted, reducing the dependence on over-generalized models and/or models trained on non-subject-specific data. The present solution can improve accuracy by accounting for inter-organ interactions, unlike typical systems that rely solely on individual organ metabolism calculations.

As will be appreciated by one skilled in the art, aspects of the present disclosure may be embodied as a system, method or computer program product. Accordingly, aspects of the present disclosure may take the form of an entirely hardware embodiment, an entirely software embodiment (including firmware, resident software, micro-code, etc.) or an embodiment combining software and hardware aspects that may all generally be referred to herein as a "circuit," "engine," "module" or "system." Furthermore, aspects of the present disclosure may take the form of a computer program product embodied in one or more computer readable medium(s) having computer readable program code embodied thereon. Aspects of the present disclosure may be implemented using one or more analog and/or digital electrical or electronic components, and may include a microprocessor, a microcontroller, an application-specific integrated circuit (ASIC), a field programmable gate array (FPGA), programmable logic and/or other analog and/or digital circuit elements configured to perform various input/output, control, analysis and other functions described herein, such as by executing instructions of a computer program product.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing. Computer program code for carrying out operations for aspects of the present disclosure may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present disclosure are described below with reference to flowchart illustrations and/or block diagrams of methods, apparatus (systems) and computer program products according to embodiments of the disclosure. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks. The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

The flowchart and block diagrams in the Figures illustrate the architecture, functionality, and operation of possible implementations of systems, methods and computer program products according to various embodiments of the present disclosure. In this regard, each block in the flowchart or block diagrams may represent a module, segment, or portion of code, which comprises one or more executable instructions for implementing the specified logical function (s). It should also be noted that, in some alternative implementations, the functions noted in the blocks may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

Reference in the specification to "one embodiment" or "an embodiment" of the present principles, as well as other variations thereof, means that a particular feature, structure, characteristic, and so forth described in connection with the embodiment is included in at least one embodiment of the present principles. Thus, the appearances of the phrase "in one embodiment" or "in an embodiment", as well any other variations, appearing in various places throughout the specification are not necessarily all referring to the same embodiment.

Figure 1B:
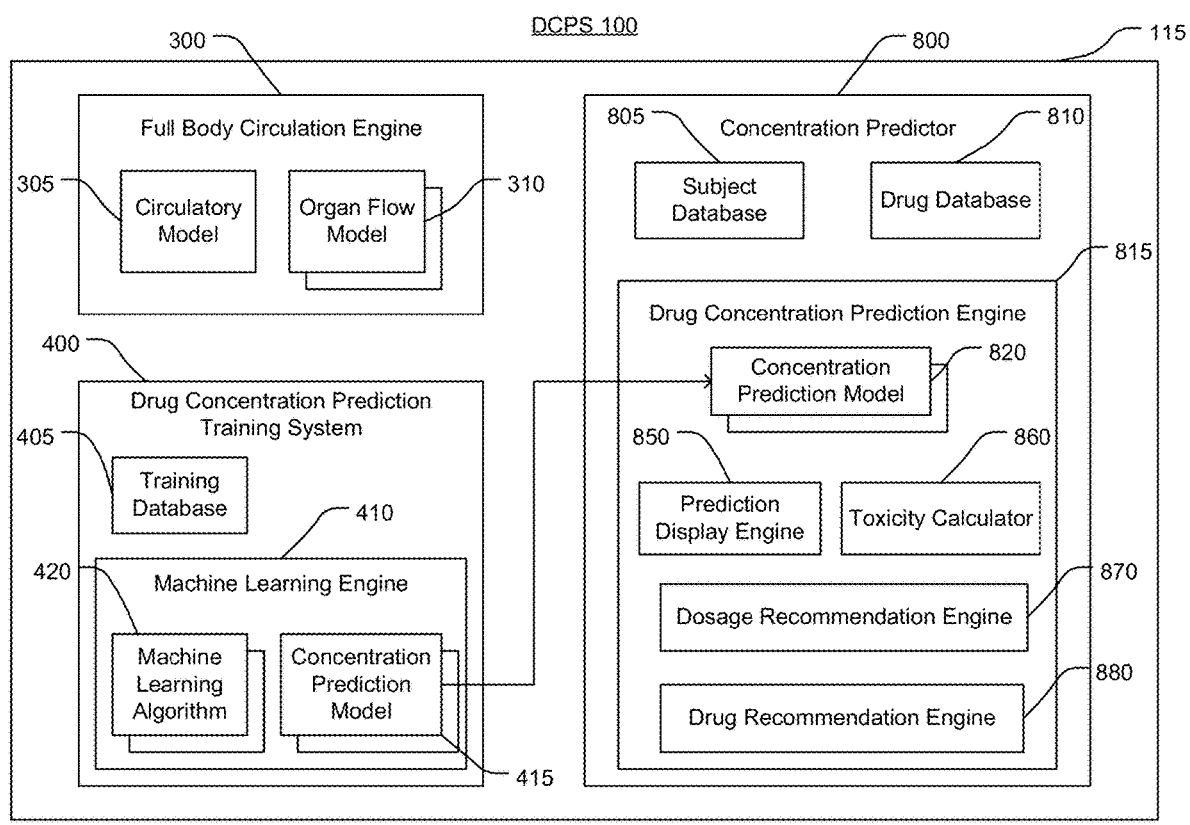
FIG. 1B is a detailed block diagram of the drug concentration prediction system of FIG. 1A further illustrating components of the full body circulation engine, drug concentration prediction training system (e.g., for extracting unknown parameters from experimental data), and concentration predictor.

Referring now to FIGS. 1A-1B, a drug concentration prediction system ("DCPS") 100 is shown according to an embodiment of the present disclosure. The DCPS 100 includes a processing circuit 105 including a processor 110 and memory 115.

In some embodiments, the DCPS 100 includes communications electronics 120. The communications electronics 120 can be configured to transmit and receive electronic signals from a remote source, such as another electronic device, a cloud server, or an Internet resource. The communications electronics 120 can be configured to communicate using any number or combination of communication standards (e.g., BLUETOOTH™, GSM, CDMA, TDNM, WCDMA, OFDM, GPRS, EV-DO, WI-FI™, WIMAX™, S02.xx, UWB, LTE™, satellite, etc). The communications electronics 120 may also include wired communications features, such as USB ports, serial ports, IEEE 1394 ports, optical ports, parallel ports, and/or any other suitable wired communication port. For example, the communications electronics 120 can receive a subject profile from a remote source and store the subject profile in subject database 805.

In some embodiments, the DCPS 100 includes a user interface device 125 including a display device 130 and a user input device 135. The display device 130 may include any of a variety of display devices (e.g., CRT, LCD, LED, OLED) configured to receive image data, such as the visualization described with reference to the prediction display engine 850, and display the image data. The user input device 135 can include various user interface elements such as keys, buttons, sliders, knobs, touchpads (e.g., resistive or capacitive touchpads), or microphones. In some embodiments, the user interface device 125 includes a touchscreen display device 130 and user input device 135, such that the user interface device 125 can receive user inputs as touch inputs and determine commands indicated by the user inputs based on detecting location, intensity, duration, or other parameters of the touch inputs.

The memory 115 includes a full body circulation engine 300, a drug concentration prediction training system ("DCPTS") 400, and a concentration predictor 800. Further aspects of the DCPS 100 will be described more detail in the following sections.

A. Systems and Methods for Full Body Circulation Model

Figure 2:
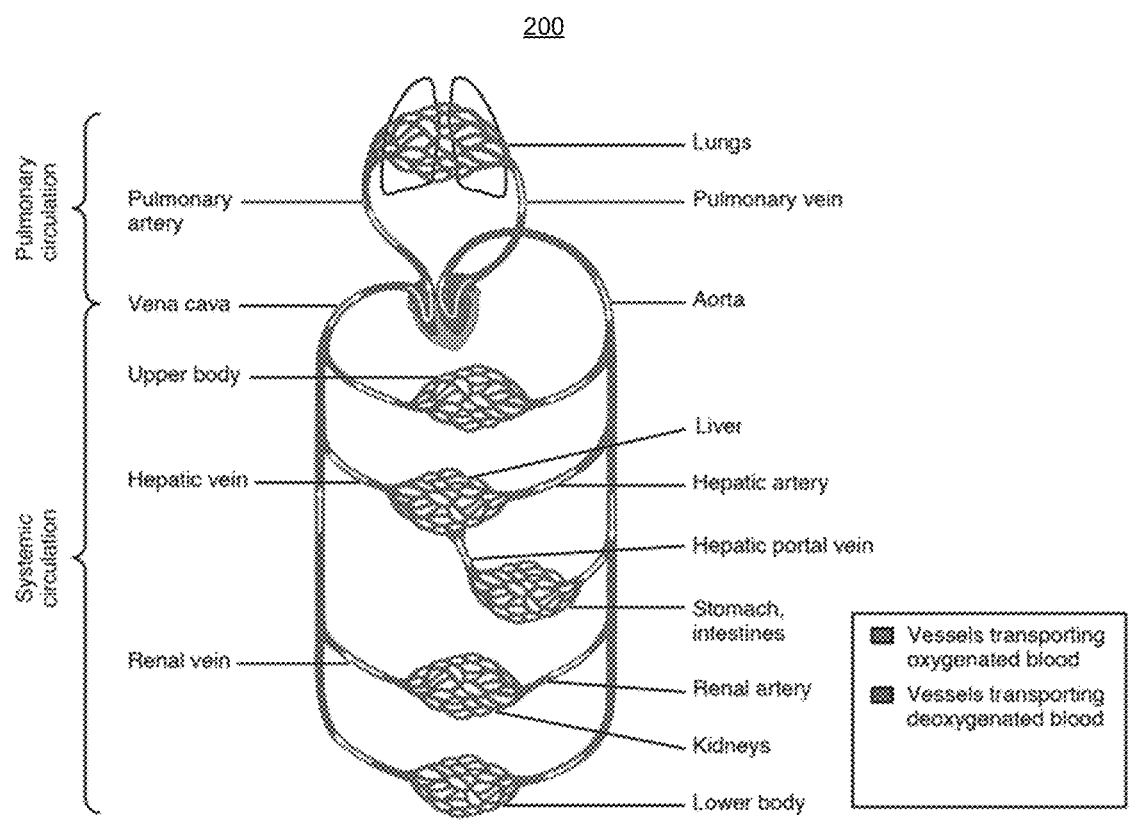
FIG. 2 is a schematic diagram of a circulatory system of a human subject, according to an embodiment of the present disclosure.

Referring now to FIG. 2, a schematic diagram of a circulatory system 200 is shown according to an embodiment of the present disclosure. In the embodiment of FIG. 2, the circulatory system 200 is illustrated for a human subject, but it will be appreciated that the DCPS 100 may also be executed for animal subjects.

Beginning with the pulmonary circulation, the pulmonary artery transports deoxygenated blood from the heart to the lungs. Gas exchange occurs to oxygenate the deoxygenated blood in the lungs (e.g., as oxygen is received due to inspiration by the subject).

For systemic circulation, oxygenated blood is then transported by the pulmonary vein to the heart, and then pumped by the heart via the aorta and other arteries of the circulatory system to various anatomical systems. For example, as shown in FIG. 2, the upper body, liver, stomach/intestines, kidneys, and lower body each represent anatomical systems (e.g., organs or other tissue groupings) which receive oxygenated blood from arteries (e.g., the hepatic artery, the renal artery), receive oxygen from the oxygenated blood, and transport deoxygenated blood back to the heart via veins (e.g., the renal vein, the hepatic vein). FIG. 2 also illustrates the hepatic portal vein transporting deoxygenated blood to the liver.

Figure 3:
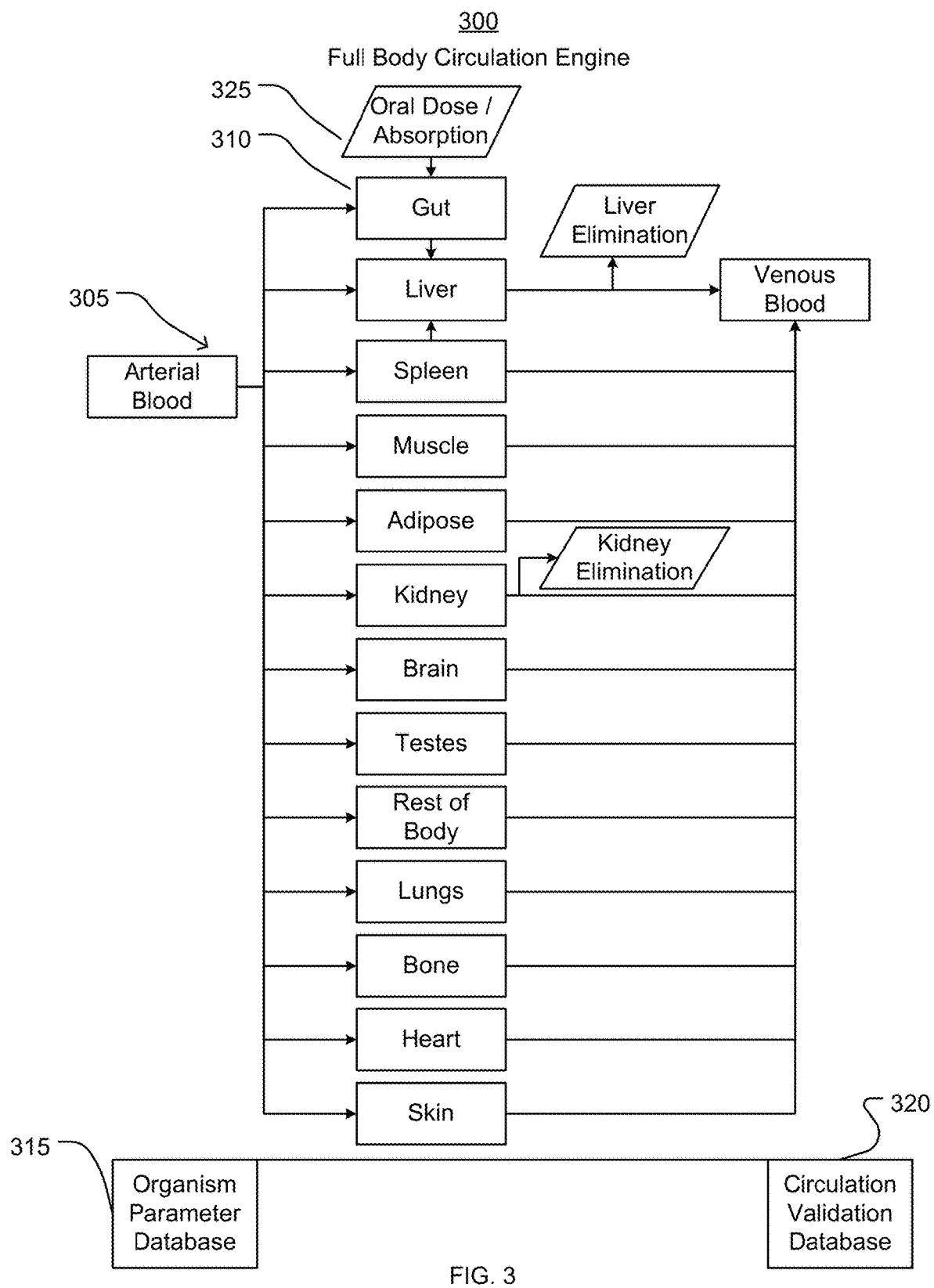
FIG. 3 is a detailed block diagram of the full body circulation engine of FIG. 1A.

Referring now to FIG. 3 and back to FIG. 1B, the full body circulation engine 300 is shown according to an embodiment of the present disclosure. The full body circulation engine 300 includes a circulatory model 305 and a plurality of organ flow models 310, in some embodiments. The full body circulation engine 300 is configured to output a representation of blood flow through the body of the subject (e.g., between organs and other anatomical systems; through organs and other anatomical systems).

The circulatory model 305 determines flow rates of blood flow through the circulatory system. For example, the circulatory model 305 can determine flow rates for blood flow between anatomical systems, such as from the heart (e.g., via arterial blood) to the liver. The circulatory model 305 can determine flow rates of blood flow based on expected blood volume and heart pumping rates for the subject.

In some embodiments, the full body circulation engine 300 includes an organism parameter database 315. The organism parameter database 315 can store organism parameters specific to a selected subject organism (e.g., human). The organism parameters can include organ volumes, organ or vessel surface areas, tissue composition, known or expected blood flow rates, and/or protein abundance. The circulatory model 305 determines flow rates for blood flow based on retrieving organism parameters from an organism parameter database 315.

The plurality of organ flow models 310 can determine blood flow rates through specific organs. In the embodiment illustrated in FIG. 3, the plurality of organ flow models 310 includes models for the guy, liver, spleen, muscle, adipose tissue, kidney, brain, testes, rest of body, lungs, bone, heart, and skin. It will be appreciated that the full body circulation engine 300 can implement as few as two organ flow models 310 (e.g., gut and liver), and may include organ flow models 310 at higher or lower levels of granularity (e.g., the gut may include distinct models for the stomach, upper intestine, and/or lower intestine).

Each organ flow model 310 can determine an output flow rate of blood flow leaving the corresponding organ based on an input flow rate of blood flow entering the corresponding organ. The organ flow model 310 may determine the output flow rate based on an expected rate of blood storage, processing, and/or absorption for the organ (e.g., output flow rate=input flow rate–rate of blood storage, processing, and/or absorption).

In some embodiments, the full body circulation engine 300 executes the circulatory model 305 and/or organ flow models 310 based on subject parameters. Subject parameters may include parameters such as age, sex, height, weight, race, ethnicity, genetic conditions, or other parameters which may be indicative of blood flow for a specific patient. Prior to validation of the full body circulation engine 300, the full body circulation engine 300 may use default or predetermined values for the subject parameters. When the full body circulation engine 300 is executed for drug concentration as will be described below in Section C, the full body circulation engine 300 may retrieve subject parameters from subject database 805.

Unlike existing systems, which may only model one anatomical system at a time, the full body circulation engine 300 can map output blood flow from a first model (e.g., circulatory model 305, a selected organ flow model 310) to a second model (and additional models as desired). It will be appreciated that the first model and second model may not be inherently configured in a similar manner; for example, different models may rely on different parameters, or may have parameters which were generated based on data from disparate subjects. The full body circulation engine 300 can train and/or validate the models 305, 310 to account for such considerations, without necessarily being privy to the underlying differences between models. As indicated by FIG. 3, the full body circulation engine 300 may represent complex blood flow paths and oxygen transfer between different anatomical systems. For example, the blood flow to each anatomical system can be affected by blood flow to and from several other anatomical systems, which may result in feedback loops and other complex relationships which are not adequately captured by existing single-model systems.

The full body circulation engine 300 can validate the circulatory model 305 and/or organ flow models 310 based on information retrieved from a circulation validation database 320. The circulation validation database 320 can store a plurality of blood flow datasets representing blood flow in various subjects. In some embodiments, each blood flow dataset maps blood flow to at least one organism parameter and/or at least one subject parameter. For example, a blood flow dataset may be structured as: {subject age; subject sex; subject weight; organ volumes; tissue composition: total blood flow rate through circulatory system; blood flow rate from heart to liver; blood flow rate from liver to heart). In some embodiments, the validation database 320 includes approximately 100 blood flow datasets.

In some embodiments, the full body circulation engine 300 validates the models 305, 310 by executing at least one of the models 305, 310 using the at least one organism and/or at least one subject parameter of a selected blood flow dataset to generate a candidate blood flow rate for the selected blood flow dataset. The full body circulation engine 300 can compare the candidate blood flow rate to the blood flow rate stored by the selected blood flow dataset to calculate a blood flow rate difference. The full body circulation engine 300 can compare the blood flow rate difference to a difference threshold, and responsive to determining that the blood flow rate difference is greater than the difference threshold, adjust at least one parameter of the models 305, 310. The full body circulation engine 300 can validate each of the circulatory model 305 and/or organ flow models 310 individually, or in combination. The full body circulation engine 300 can execute an optimization algorithm to adjust the at least one parameter of the models 305, 310 until an optimization condition is satisfied (e.g., a measure of differences between the candidate blood flow rates for each blood flow dataset and the stored blood flow rates is minimized).

B. Systems and Methods for Training a Drug Concentration Prediction Model

Figure 4:
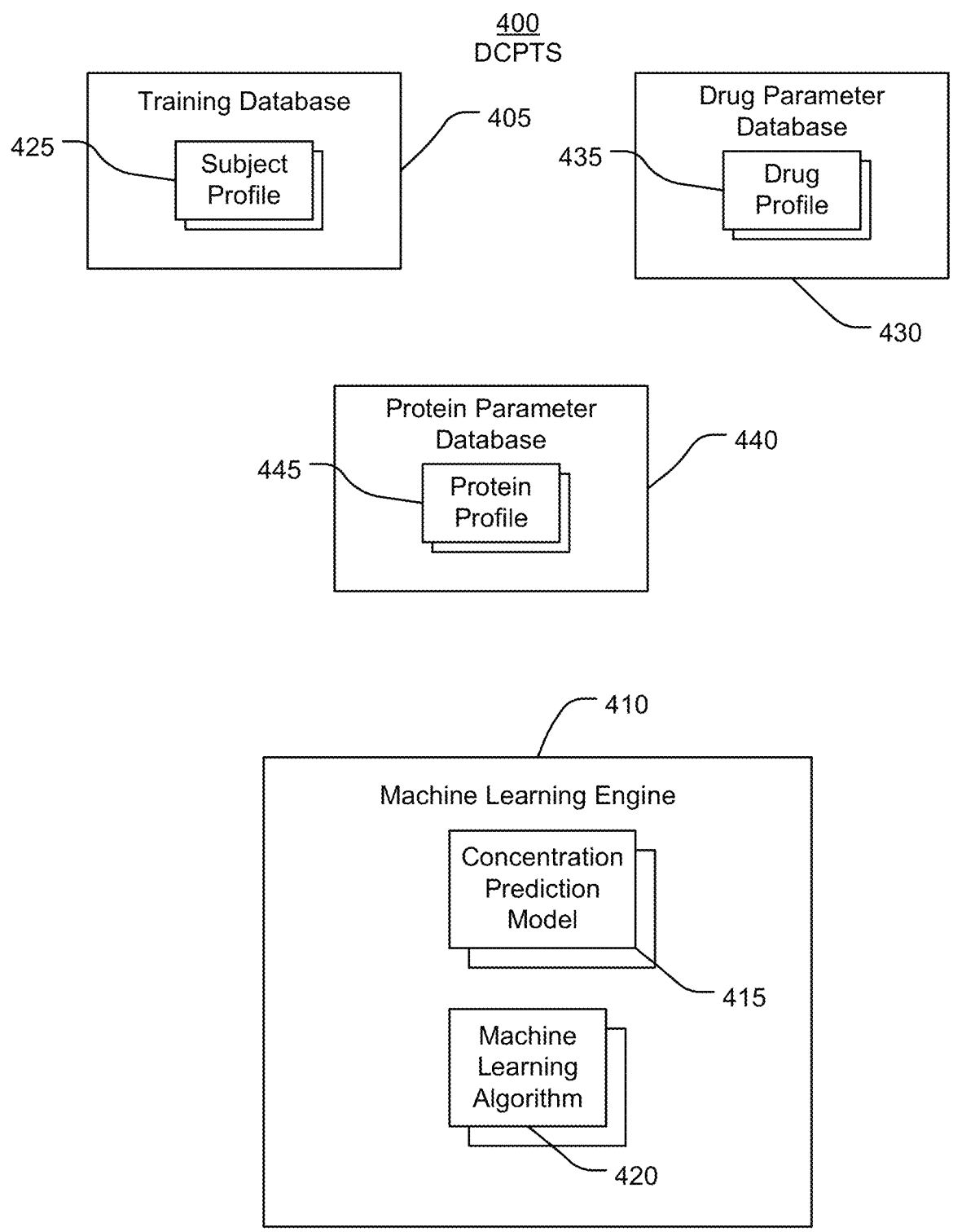
FIG. 4 is a detailed block diagram of the drug concentration prediction training system of FIG. 1A.

Referring to FIG. 4 and back to FIG. 1B, the DCPTS 400 is shown according to an embodiment of the present disclosure. The DCPTS 400 includes a training database 405 and a machine learning engine 410. The machine learning engine 410 includes a drug concentration prediction model 415 and at least one machine learning algorithm 420.

The training database 405 includes a plurality of subject profiles 425. Each subject profile 425 can represent a training data (e.g., vector of training information) to be used to train the drug concentration prediction model 415. For example, the subject profile 425 can include one or more drug concentrations as a function of time. In some embodiments, each subject profile 425 includes at least one subject characteristic and a corresponding known drug dosage. Each subject profile 425 may include a plurality of known drug concentrations (as a function of time) corresponding to the at least one subject characteristic. The subject profile 425 may also include a drug identifier (e.g., name or structural representation of drug) having the known drug concentration(s). As an illustrative example, the subject profile 425 can be organized as {drug identifier, drug concentration, time, subject sex}.

The at least one subject characteristic can include similar characteristics as the subject parameters described with reference to the full body circulation engine 300, such as age, sex, height, weight, race, ethnicity, genetic conditions, or other similar parameters. As indicated by the example above, the subject profile 425 may not necessarily include every subject characteristic (if any).

The at least one drug characteristic may include the drug identifier, as well as other drug characteristics such as a classification of the drug. The at least one drug characteristic may include at least one drug-dependent parameter, such as solubility, blood cell and/or plasma protein binding (e.g., fraction unbound in plasma, "$f_{u,p}$"), lipophilicity, effective molecular weight, pKa, permeability coefficient, partition coefficient such as blood plasma partitioning ("[B:P]"), transporter contribution to drug disposition, and/or in vitro data regarding metabolism of the drug by hepatic or ex-hepatic enzymes (e.g., intrinsic clearance, "$CL_{int}$"), and other such parameters.

In some embodiments, the subject profiles 425 of the training database 405 may include few, if any, drug characteristics. For example, as indicated by the example above, the subject profile 425 only includes the drug identifier. The DCPTS 400 may include a drug parameter database 430 including a plurality of drug profiles 435. Each drug profile 435 may map the drug identifier to one or more drug-dependent parameters. Various drug profiles 435 may include fewer or greater drug-dependent parameters, depending on known information regarding each drug in the drug parameter database 430.

The machine learning engine 410 includes a plurality of drug concentration prediction models 415 associated with each anatomical system to be modeled. For example, each drug concentration prediction model 415 can correspond to one of the models 305, 310 of the full body circulation engine 300. Each drug concentration prediction model 415 can receive an initial drug concentration (e.g., of an input blood flow entering the anatomical system) and generate a predicted drug concentration (e.g., of blood within the anatomical system; of an output blood flow exiting the anatomical system) at a point in time.

The drug concentration prediction models 415 may execute physiologically based pharmacokinetic ("PBPK") models. Each drug concentration prediction model 415 may include at least one submodel, which may be used to represent functionality of lower level systems, such as protein behavior. For example, the drug concentration prediction model 415 for the liver may include a submodel to represent cytochrome P450 ("CYP") functionality. The submodels may be validated and/or trained independently of the higher level drug concentration prediction model 415.

In some embodiments, the DCPTS 400 includes a protein parameter database 440 storing a plurality of protein profiles 445. Each protein profile 445 includes a protein identifier. Each protein profile 445 may include a structural representation of the associated protein. Each protein profile 445 may include one or more protein parameters, which may represent functional activity of the protein. Protein parameters may be used to represent proteins function as drug metabolites, transporter proteins, and enzymes.

The machine learning engine 410 can execute the full body circulation engine 300 to determine respective blood flow rates for blood flow to/from each drug concentration prediction model 415. The machine learning engine 410 can use the respective blood flow rates to determine drug concentration of blood flow exiting a particular anatomical system, and thus determine drug concentration of blood flow entering any downstream anatomical system. For example, referring back to FIG. 3, the machine learning engine 410 can identify a first drug dosage 325 based on the subject profile 425 or any other information indicating a drug dosage being received by the subject. The machine learning engine 410 can execute the full body circulation engine 300 to determine a first blood flow rate entering the gut and a second blood flow rate exiting the gut and entering the liver. The machine learning engine 410 can execute the drug concentration prediction model 415 corresponding to the gut to determine the drug concentration in the second blood flow rate entering the liver, and thus use the drug concentration of the second blood flow rate when executing the drug concentration prediction model 415 for the liver.

Each drug concentration prediction model 415 uses at least one drug characteristic to calculate the predicted drug concentration. As an illustrative example, a drug concentration prediction model 415 for a selected organ may use a partition coefficient and an intrinsic clearance coefficient for a selected drug to calculate drug concentration as a function of time for the selected drug in the selected organ. In some embodiments, the drug concentration prediction model 415 retrieves the at least one drug characteristic from the subject profile 425. In some embodiments, the drug concentration prediction model 415 retrieves the at least one drug characteristic from the drug profile 435 corresponding to the selected drug.

The machine learning engine 410 can determine drug concentrations as a function of time for a plurality of anatomical systems. The machine learning engine 410 can select a subject profile 425, and retrieve a drug identifier from the subject profile 425 to identify the drug for which concentration is to be determined. The machine learning engine 410 can execute a plurality of the drug concentration prediction models 415 based on the identified drug to calculate a plurality of predicted drug concentrations. The machine learning engine 410 can retrieve the time stored in the subject profile 425 (and associated with the known concentration stored in the subject profile 425), and execute the plurality of drug concentration prediction models 415 to output predicted drug concentrations at the retrieved time, so that the predicted drug concentrations match the known drug concentrations.

The machine learning engine 410 compares each of the predicted drug concentrations to the corresponding known drug concentration to generate a comparison result. For example, the machine learning engine 410 can perform a subtraction (e.g., an absolute value subtraction) to determine the comparison result. The comparison result may indicate how accurately the drug concentration prediction models 415 are able to predict drug concentrations.

The machine learning engine 410 determines whether the comparison results satisfy a comparison condition. For example, the machine learning engine 410 can execute an optimization algorithm to reduce or minimize the comparison result based on adjusting parameters of the drug concentration prediction models 415. In some embodiments, responsive to the comparison result not satisfying the comparison condition, the machine learning engine 410 adjusts one or more parameters for at least one of the drug concentration prediction models 415. Responsive to the comparison result satisfying the comparison condition, the machine learning engine 410 can output the plurality of drug concentration prediction models 415, or store the plurality of drug concentration prediction models 415 with an indication that the drug concentration prediction models 415 have been trained.

In some embodiments, the machine learning engine 410 executes at least one drug prediction model 415 (or a submodel thereof) using a corresponding machine learning algorithm 420. Various machine learning algorithms 420 (and associated optimization algorithms) may be executed, depending on the characteristics of the drug prediction model 415, such as which parameters are unknown or inaccurately represented for the drug prediction model 415. For example, the machine learning engine 410 can use gradient descent; the machine learning engine 410 can execute clustering algorithms, such as K-means clustering; the machine learning engine 410 can execute principal component analysis (PCA) or independent component analysis (ICA), such as to identify one or more key parameters and modify values for the one or more key parameters.

In some embodiments, the machine learning algorithms 420 includes a neural network. The neural network can include a plurality of layers each including one or more nodes, such as a first layer (e.g., an input layer), a second layer (e.g., an output layer), and one or more hidden layers. The neural network can include characteristics such as weights and biases associated with computations that can be performed between nodes of layers. The machine learning engine 410 can train the neural network by providing the subject profiles 425 to the input layer, receiving output from the output layer which represents the predicted drug concentration, and comparing the predicted drug concentration to the known drug concentration to generate the comparison result.

As described above, the machine learning engine 410 can execute an optimization algorithm to reduce or minimize the comparison result, so that the drug concentration prediction model 415 more accurately represents the known drug concentrations. With respect to the neural network, the machine learning engine 410 can use the optimization algorithm to modify the weights and/or biases of the neural network so that the drug concentration prediction model 415 which uses the neural network more accurately represents the physiological behavior of the corresponding anatomical system (e.g., for drug absorption and transport).

In an embodiment, the machine learning engine 410 uses a neural network to model a CYP protein. The machine learning engine 410 can retrieve the structural representation of the CYP protein from the protein parameter database 440 (e.g., from a protein profile 445 corresponding to the CYP protein), provide the structural representation to the input layer of the neural network, and receive an output from the output layer of the neural network, the output representing a protein parameter, such as a function performed by the CYP protein. The machine learning engine can compare the output to the output stored in the protein profile 445 for CYP to generate the comparison result, and execute an optimization algorithm to reduce or minimize the comparison result so that the neural network more accurately represents functionality of the CYP protein.

In some embodiments, the machine learning algorithms 420 include a classification and/or regression algorithm, such as a support vector machine ("SVM"). The SVM can be configured to calculate a hyperplane or set of hyperplanes representative of parameters of the drug concentration prediction model 415 being trained. For example, the machine learning engine 410 can receive a plurality of subject profiles 425 which may include drug concentration values at various points in time (which may not necessarily be the same points in time); the subject profiles 425 may also include certain subject parameters, though the subject parameters included may not be the same in each subject profile 425. The drug concentration prediction model 415 represented by the SVM may be configured to calculate drug concentration as a function of time based on a variety of parameters, including subject parameters and/or drug parameters. The parameters of the SVM may not necessarily be known, or may be inaccurate for the selected drug, or for a particular subject group.

For each subject profile 425 (e.g., each pair of time/known drug concentration points of the subject profile 425), the machine learning engine 410 can cause the SVM to calculate a proposed drug concentration using the drug concentration prediction model 415. The SVM execute an optimization algorithm, such as gradient descent, to reduce or minimize differences between the proposed drug concentrations and corresponding known drug concentrations by adjusting the drug parameters of the hyperplane.

As an example, determining a value for a partition coefficient for drug metabolism between the venous blood and the liver for a specific drug, such as acetaminophen ("APAP"), may be crucial for accurately generating the drug concentration prediction model 415 for the liver and representing clearance values of APAP from the liver. However, it is typically difficult to measure the partition coefficient, as a clear relationship between drug concentration and the partition coefficient cannot be easily extracted from experimental data. The machine learning engine 410 can execute the SVM using the experimental data of the subject profiles 425 to calculate a hyperplane (including a parameter representative of the partition coefficient) which accurately models the experimental data, thus providing a value for the partition coefficient which is more accurate than existing models.

Referring briefly to FIGS. 5A-5E, various charts of drug concentrations as functions of time are illustrated for experimental data and predicted drug concentrations generated by the DCPTS 400.

Figure 5A:
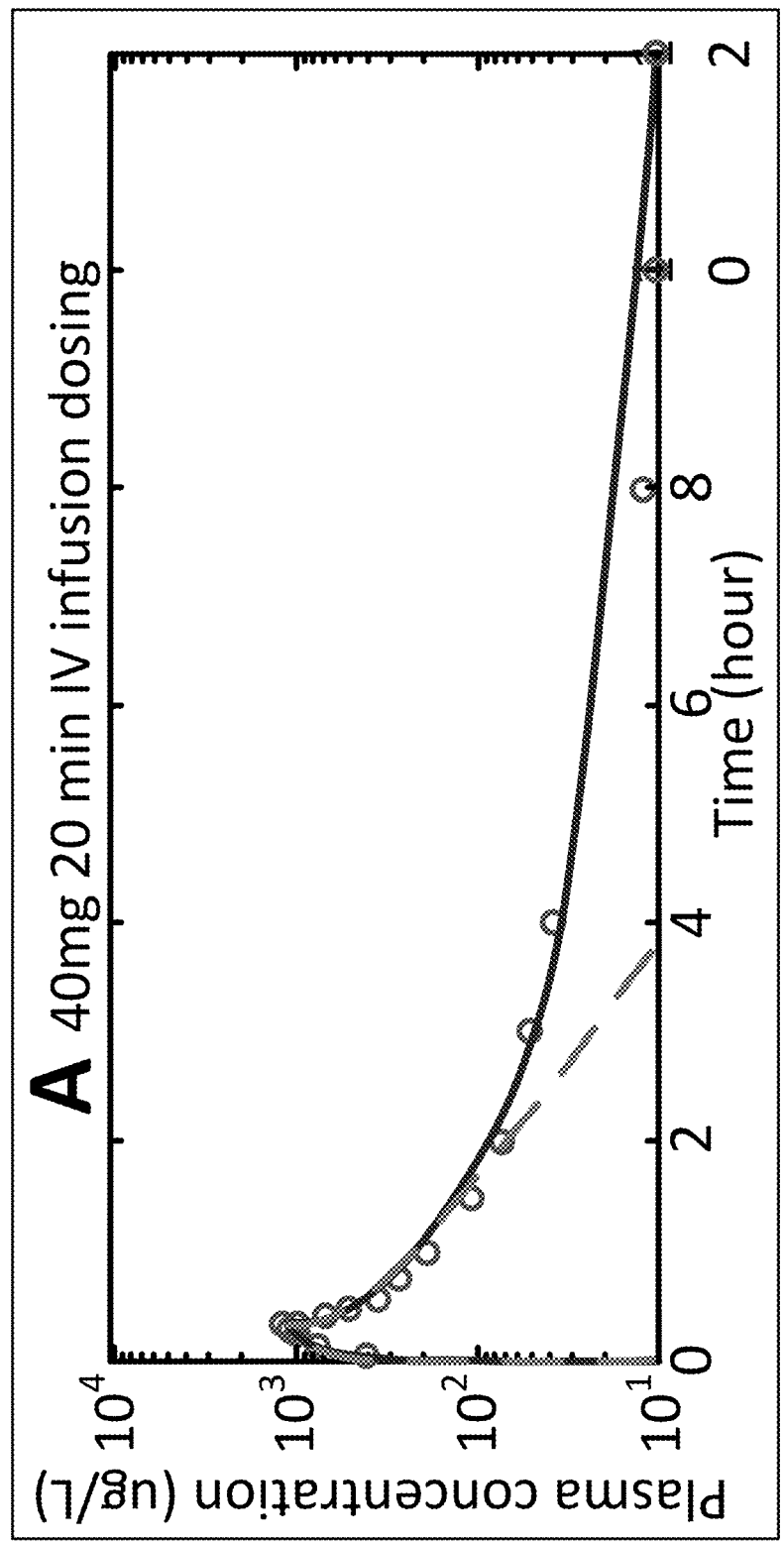
FIGS. 5A-5E are charts of known and predicted drug concentrations, according to an embodiment of the present disclosure.
Figure 5B:
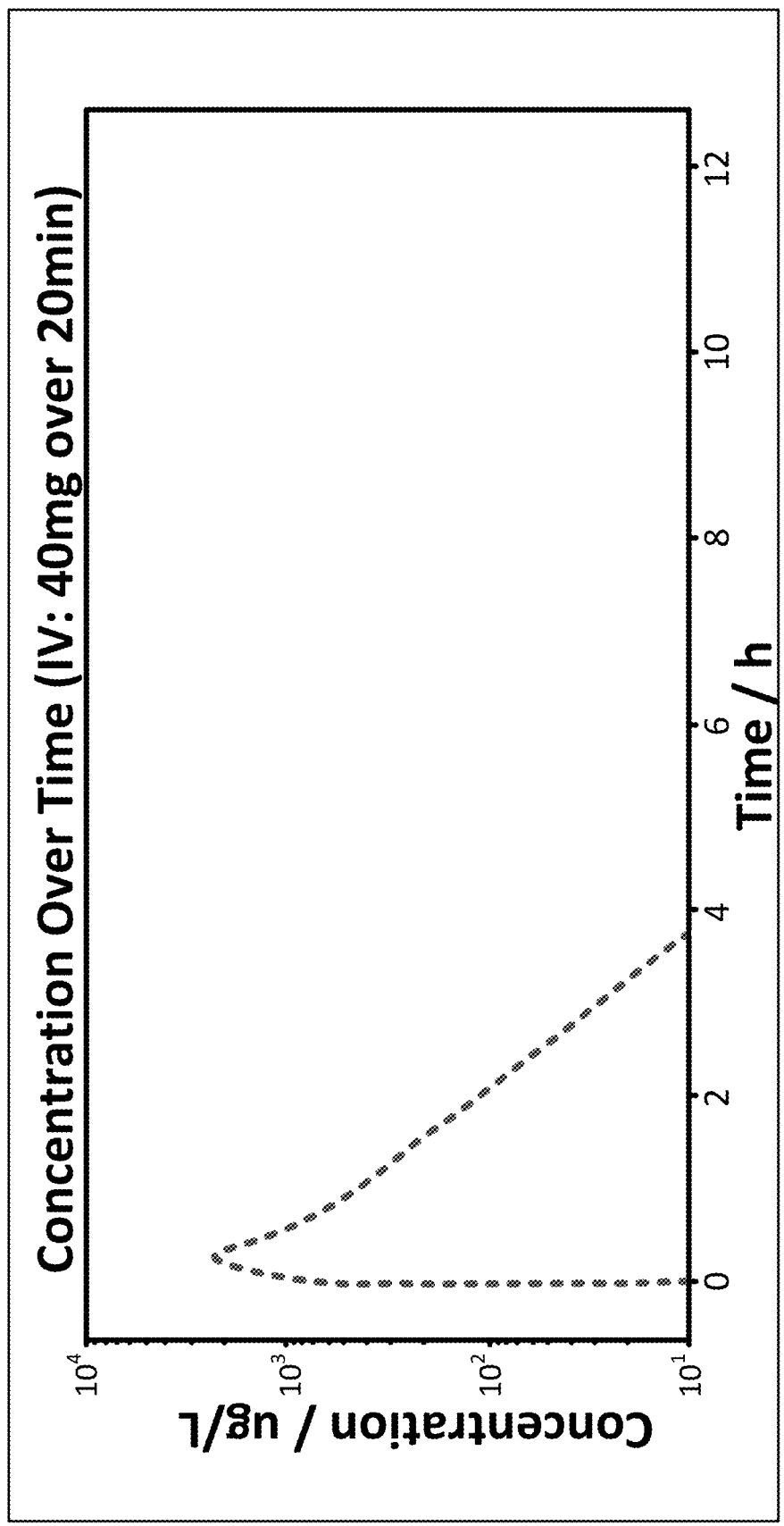

FIG. 5A illustrates known drug concentration (in plasma) as a function of time from experimental data of a 40 mg, 20 minute intravenous infusion of a selected drug. FIG. 5B illustrates predicted drug concentration (in plasma) as a function of time, generated by the DCPTS 400 after having been trained (and/or using concentration predictor 800), also for a 40 mg, 20 minute intravenous infusion of the selected drug. As shown in FIGS. 5A and 5B, the drug concentration values predicted by the DCPTS 400 have similar values at similar points in time (e.g., the drug concentrations in both charts peak between 0 and 1 hour, at a value slightly above 1000 ug/L).

It will be appreciated that the known drug concentrations as a function of time shown in FIG. 5A may be represented in a corresponding subject profile 425 of FIG. 4. As such, if the DCPTS 400 were being trained based on the subject profile 425 data of FIG. 5A, the differences between the predicted drug concentration values of FIG. 5B and the known drug concentration values of FIG. 5A could be used to modify the parameters of the drug concentration prediction models 415 of the DCPTS 400.

Figure 5C:
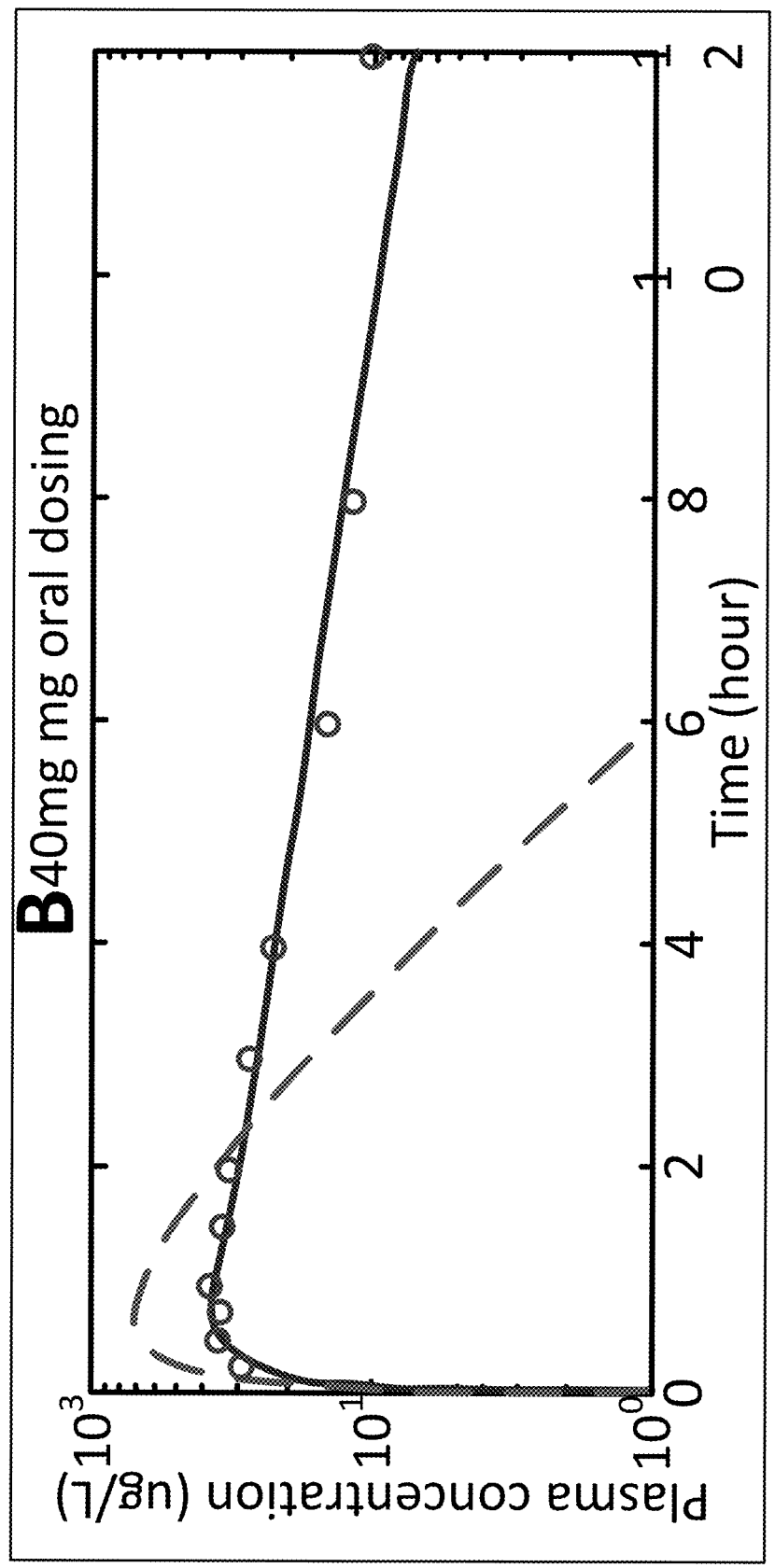
Figure 5D:
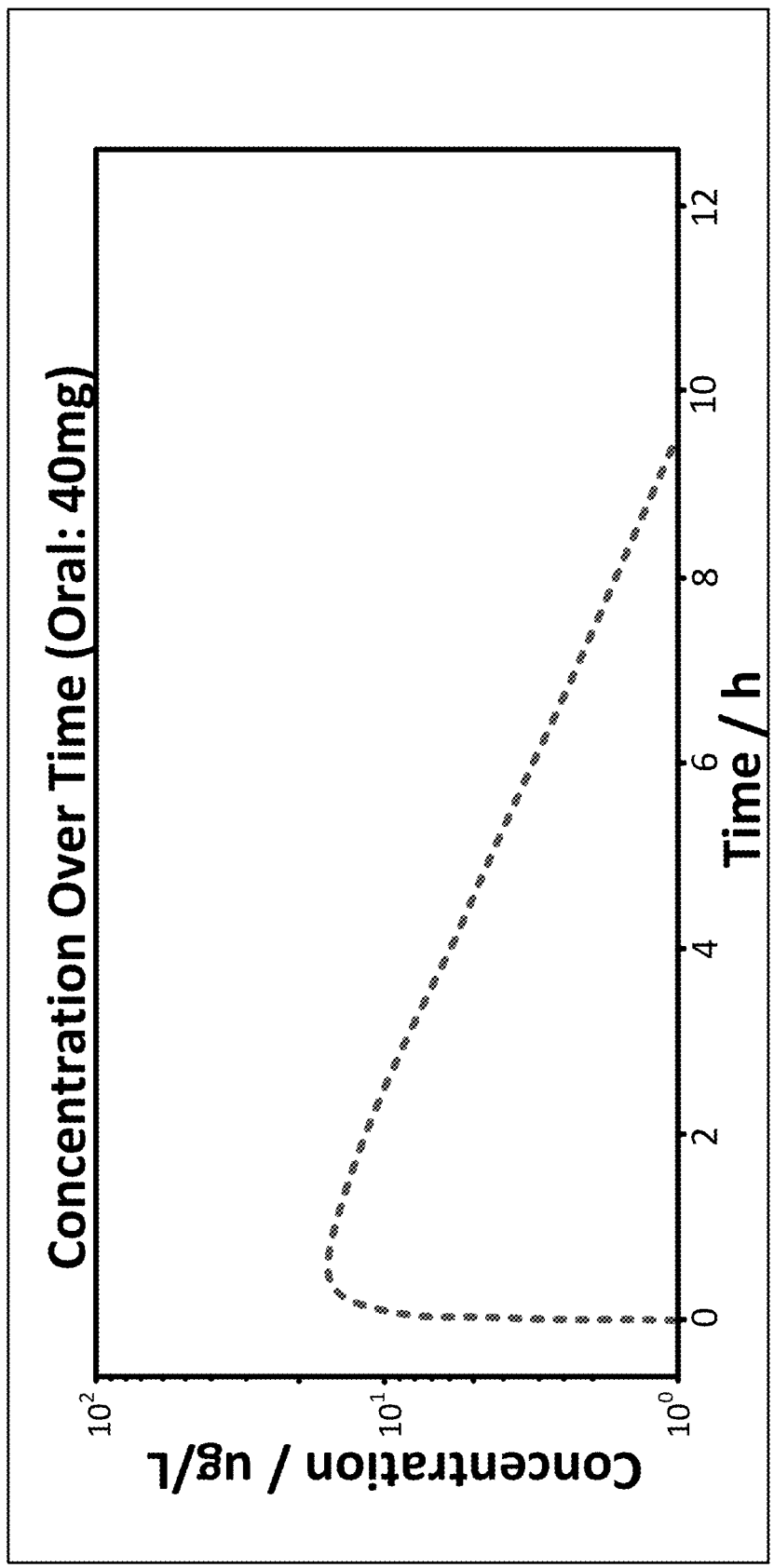

Similarly, FIG. 5C illustrates known drug concentrations as a function of time for a 40 mg oral dosing, and FIG. 5D illustrates predicted drug concentrations as a function of time for a 40 mg oral dosing. Again, the predicted drug concentration values has a similar profile as to the known drug concentration values.

Figure 5E:
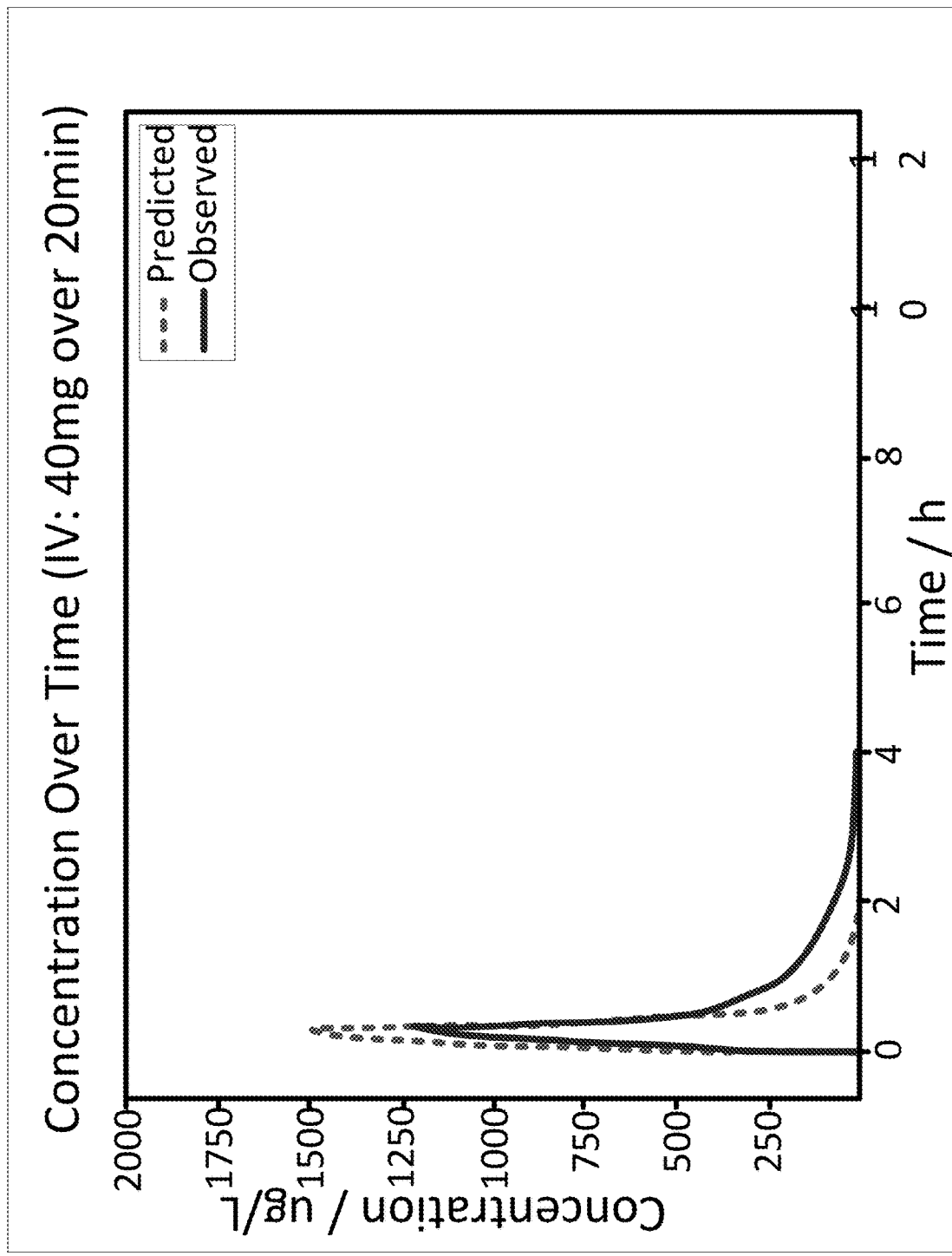
Figure 6:
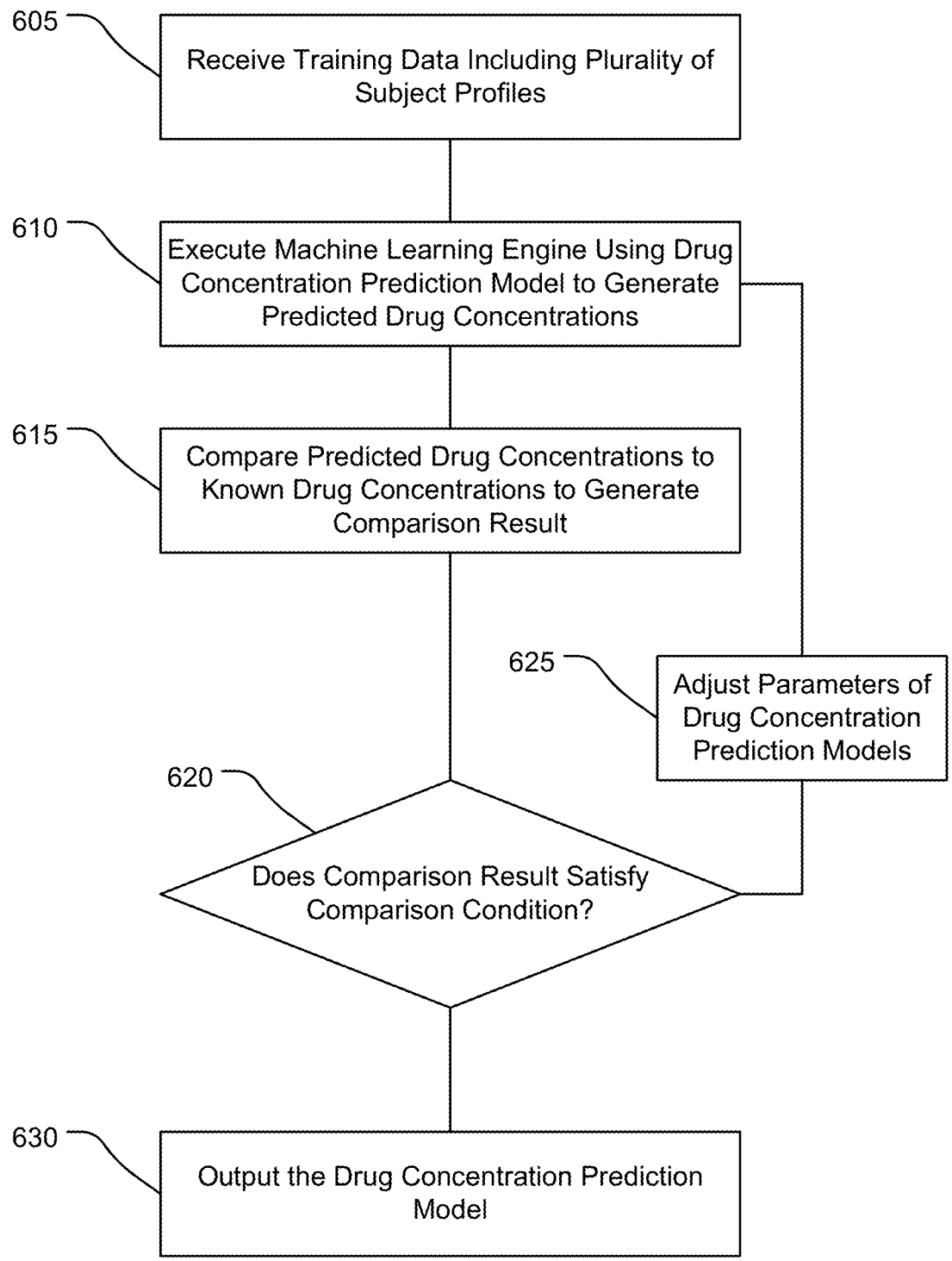
FIG. 6 is a flow diagram of a method for training a drug concentration prediction model, according to an embodiment of the present disclosure.

Referring now to FIG. 5E, known ("observed") drug concentration over time is compared to predicted drug concentration over time as generated by the trained DCPTS 400. In the example shown in FIG. 5E, the area under curve ("AUC") for the predicted and known drug concentrations are accurate to 85%. As such, the present solution can enable more accurate drug concentration predictions than existing systems by Referring now to FIG. 6, a method 600 for training a full body circulation and drug concentration prediction system is shown according to an embodiment of the present disclosure. The method 600 can be executed using various systems described herein, such as the full body circulation engine 300 and DCPTS 400.

At 605, training data is received including a plurality of subject profiles. The subject profile can include one or more drug concentrations as a function of time. In some embodiments, each subject profile includes at least one subject characteristic and a corresponding known drug concentration. Each subject profile may include a plurality of known drug concentrations (as a function of time) corresponding to the at least one subject characteristic. The subject profile may also include a drug identifier (e.g., name or structural representation of drug) having the known drug concentration (s). As an illustrative example, the subject profile can be organized as {drug identifier, drug concentration, time, subject sex}. The at least one subject characteristic can include similar characteristics as the subject parameters described with reference to the full body circulation engine 300, such as age, sex, height, weight, race, ethnicity, genetic conditions, or other similar parameters. As indicated by the example above, the subject profile may not necessarily include every subject characteristic (if any).

At 610, a machine learning engine is executed using the plurality of subject profiles. The machine learning engine includes at least one drug concentration prediction model which includes a plurality of drug parameters. The drug concentration prediction model generates a predicted drug concentration based on the plurality of drug parameters and the corresponding at least one subject characteristic. The drug concentration can be predicted based on an initial drug concentration for the anatomical system being represented by each drug concentration prediction model.

At 615, the predicted drug concentration is compared to the known drug concentration (from the subject profile) to generate a comparison result. At 620, the machine learning engine determines if the comparison result satisfies a comparison condition, such as by executing an optimization algorithm using the comparison result. In some embodiments, the machine learning engine determines if the comparison result satisfies the comparison condition by comparing a difference between the predicted drug concentration and the known drug concentration to a threshold difference, and determining that the difference is less than the threshold difference.

If the comparison result does not satisfy the comparison condition, then at 625, the parameters of the at least one drug concentration prediction model are adjusted (e.g., using the optimization algorithm). If the comparison result satisfies the comparison condition, then at 630, the drug concentration prediction model (now trained) is outputted (e.g., transmitted to another module; stored with an indication of having been trained).

Figure 7:
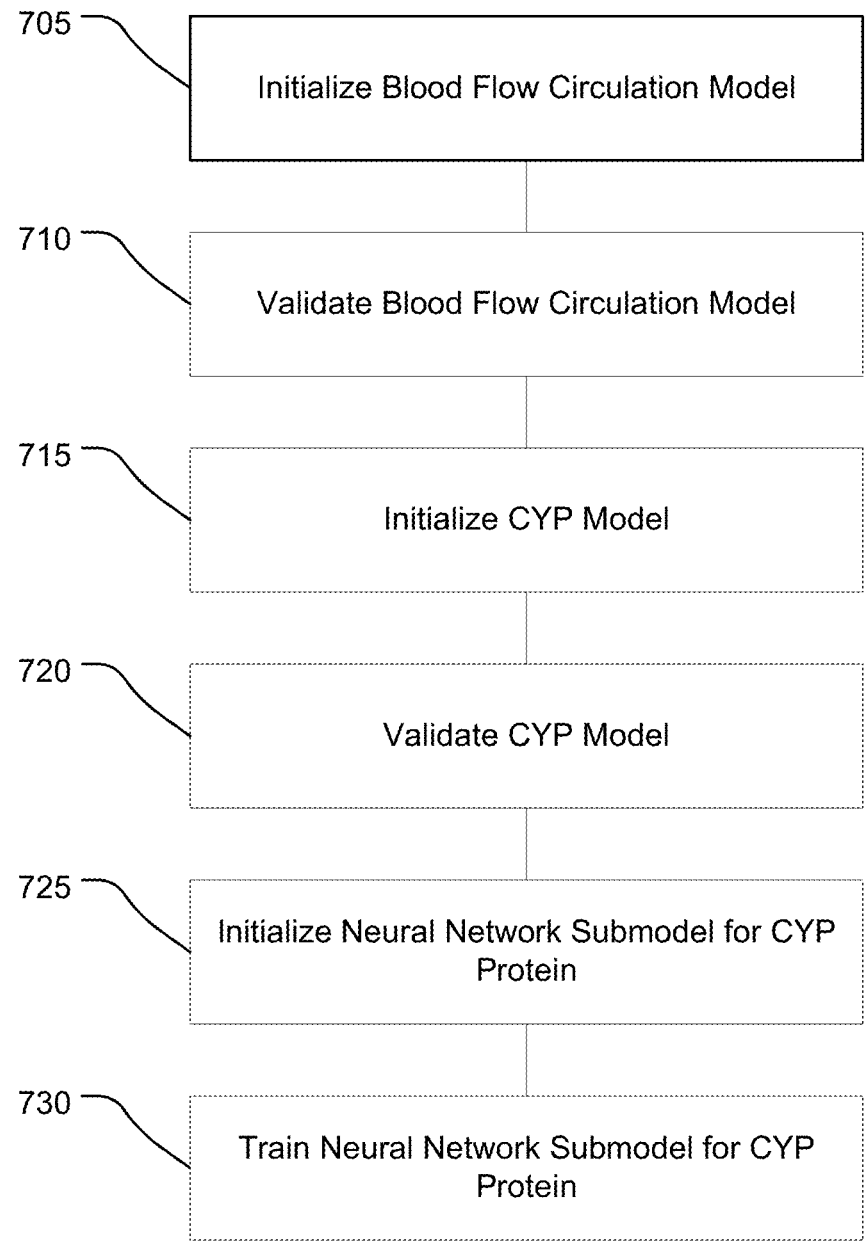
FIG. 7 is a flow diagram of a method of training a drug concentration prediction model for the liver, according to an embodiment of the present disclosure.

Referring now to FIG. 7, a method 700 of training a drug concentration prediction model for the liver, the drug concentration prediction model including a including a neural network submodel for representing a CYP protein, is shown according to an embodiment of the present disclosure. The method 700 can be executed using various systems described herein, such as the full body circulation engine 300 and DCPTS 400.

At 705, a blood flow circulation model including a circulatory model and a plurality of organ flow models is initialized. The plurality of organ flow models includes a model for blood flow in the liver. Initializing the blood flow circulation model can include initializing the blood flow circulation model using subject parameters such as age, sex, or weight, and/or using organism parameters such as organ volumes, surface areas, tissue composition, known blood flow rates, and/or protein abundance.

At 710, the blood flow circulation model is validated. Validating the blood flow circulation model can include comparing blood flow rates generated by the blood flow circulation model to known blood flow rates. In some embodiments, validating the blood flow circulation model includes adjusting parameters of the blood flow circulation model to reduce a difference between the blood flow rates generated by the model and the known blood flow rates.

At 715, a CYP model including a plurality of drug interaction parameters is initialized. The drug interaction parameters can be drug depending parameters representing bonding or other chemical interaction between the selected drug and CYP proteins. The CYP model can output a concentration of unbound toxins in the liver as a function of time.

At 720, the CYP model is validated. Validating the CYP model can include comparing the modeled concentrations of unbound toxins in the liver over time to known concentrations of unbound toxins (which may be retrieved from subject profiles or other validation databases based on experimental data). In some embodiments, validating the CYP model includes adjusting parameters of the CYP model to reduce a difference between the modeled concentrations of unbound toxins and the known concentrations of unbound toxins.

At 725, a neural network submodel for a CYP protein is initialized. The neural network submodel may be initialized using a structure of the CYP protein.

At 730, the neural network submodel is trained based on CYP training data. The CYP training data may include known function data regarding the CYP protein (e.g., toxin binding rates). The neural network may be trained by executing an optimization algorithm which adjusts weights and/or biases of the neural network to reduce a difference between the function data outputted by the neural network submodel and the known function data. It will be appreciated that the neural network submodel may be trained prior to validation of the CYP model and/or the blood flow circulation model, such that the higher level toxin binding functions represented by the CYP model may be dependent on the lower level functions of the CYP neural network submodel. Training the neural network submodel before validation may improve the accuracy of the drug concentration prediction model and/or reduce the computational burden required to accurately generate the drug concentration prediction model.

Figure 8:
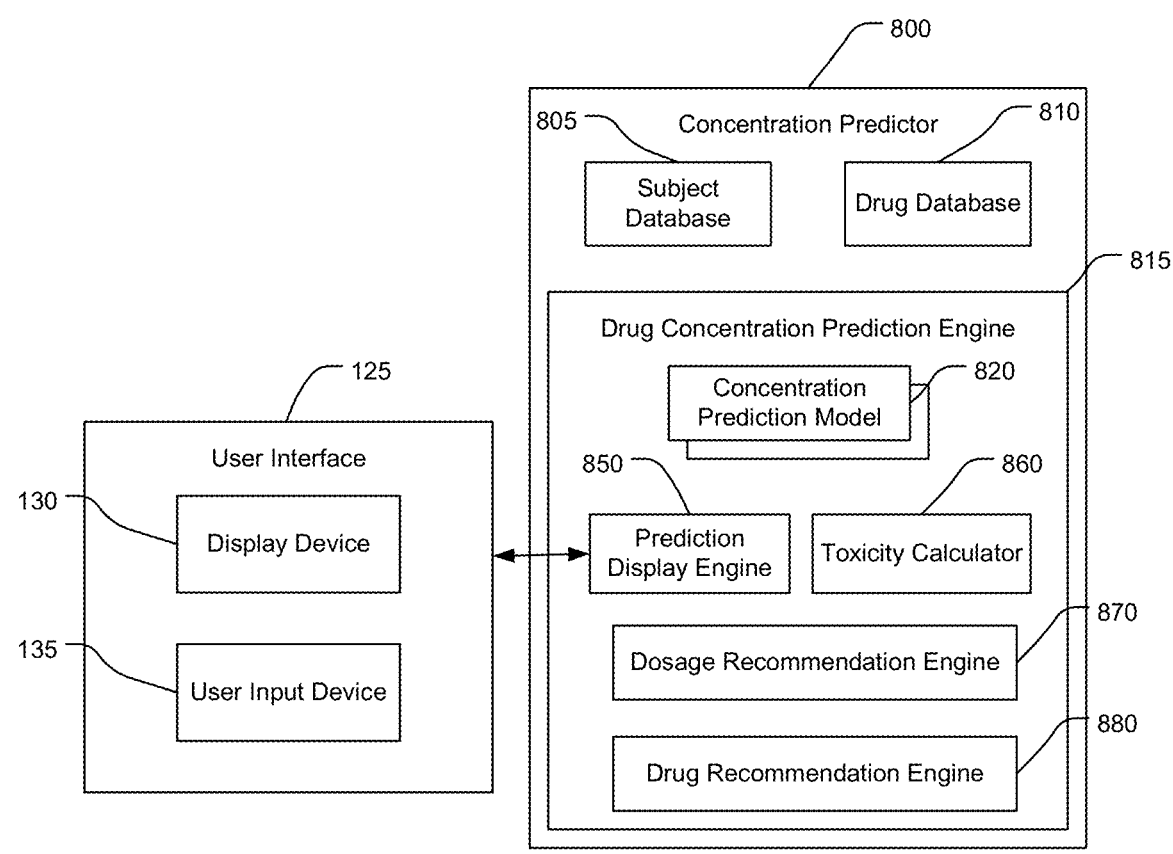
FIG. 8 is a detailed block diagram of the concentration predictor of FIG. 1A.

C. Systems and Methods for Predicting Drug Concentrations Using a Drug Concentration Prediction Model Referring now to FIG. 8 and back to FIG. 1B, a concentration predictor 800 is shown according to an embodiment of the present disclosure. The concentration predictor 800 includes a subject database 805, a drug database 810, and a drug concentration prediction engine 815. As shown in FIG. 1B, the drug concentration prediction engine 815 includes a plurality of drug concentration prediction models 820, which can be trained versions of the drug concentration prediction models 415 of the DCPTS 400.

The subject database 805 includes at least one subject characteristic of a subject for which a drug concentration is to be predicted. The at least one subject characteristic of the subject database 805 can be similar to the at least one subject characteristic of the training database 405.

The drug database 810 includes at least one drug characteristic of a drug to be administered to the subject. The drug database 810 can include similar information (e.g., parameters) as the drug parameter database 430.

In some embodiments, the concentration predictor 800 executes the full body circulation engine 300 by initializing the full body circulation engine 300 using the at least one subject characteristic. For example, the drug concentration engine 815 can retrieve the at least one subject characteristic from the subject database 805 and provide the at least one subject characteristic to the full body circulation engine 300. Using the full body circulation engine 300, the concentration predictor 800 can determine blood flow rates in the circulatory system and between various anatomical systems. As noted above with respect to FIG. 3, it will be appreciated that the full body circulation engine 300 can model blood flow rates (and associated drug concentrations) throughout the circulatory system in a more accurate manner than existing systems that do not account for complex blood flow relationships between anatomical systems.

Using the full body circulation engine 300 and the at least one drug characteristic, the drug concentration prediction engine 815 can determine a first concentration of the drug in a first blood flow entering a first organ. The drug concentration prediction engine 815 can receive an indication of a drug dosage (e.g., dosage 325 as shown in FIG. 3) and use the indication of the drug dosage to predict the first concentration of the drug.

The drug concentration prediction engine 815 can determine the drug concentrations as a function of time (e.g., at any selected time). The drug concentration engine 815 can determine the drug concentration level at various locations in the subject (e.g., in the circulatory system, in various organs or other anatomical systems) at the selected time.

The drug concentration prediction engine 815 can initialize a first drug concentration model 820 (e.g., corresponding to the first organ) using the first concentration of the drug. The drug concentration prediction engine 815 can determine, using the first drug concentration model 820, a second concentration of the drug in the first organ. For example, the drug concentration engine 815 can cause the first drug concentration model 820 to output an indication of drug concentration in the first organ at a selected point in time.

In some embodiments, the drug concentration prediction engine 815 modifies the first drug concentration model 820 using the at least one subject characteristic. The drug concentration prediction engine 815 can modify the first drug concentration model 820 prior to determining the second concentration of the drug. The drug concentration prediction engine 815 can modify the first drug concentration model 820 to make the first drug concentration model 820 more accurately predict the second concentration of the drug. The drug concentration prediction engine 815 can modify the first drug concentration model 820 by selecting the first drug concentration model 820 from among a plurality of pre-determined drug concentration models 820 based on the at least one subject characteristic. For example, if the at least one subject characteristic includes an age of the subject, the drug concentration prediction engine 815 can compare the age of the subject to an age (or age range) assigned to each of the plurality of pre-determined drug concentration models 820, and select the pre-determined drug concentration model 820 having an assigned age that matches the age of the at least one subject characteristic. The drug concentration prediction engine 815 can modify the first drug concentration model 820 by modifying a subject characteristic-dependent parameter of the first drug concentration model 820. For example, if the at least one subject characteristic includes the age of the subject, the drug concentration prediction engine 815 can modify an age-dependent parameter of the first drug concentration model 820 (e.g., if the first drug concentration model 820 is of the form $A=A_0 * \exp(-k*t)$, where $A_0$ is the initial drug concentration, A is the drug concentration at time t, and k is an age-dependent parameter, the drug concentration prediction engine 815 can modify the value of the parameter k based on the age of the subject). The drug concentration prediction engine 815 can modify the subject-dependent parameter using a parameter mapping function (which may be trained based on subject data regarding a plurality of subjects, such as by using a regression model or other training operations described with reference to the DCPTS 400). By modifying the first drug concentration model 820 to be more specific to the subject based on the at least one subject characteristic, the drug concentration prediction engine 815 can more accurately determine the second concentration of the drug, such as by reducing dependence on over-generalized models that may have been constructed using subject data having relatively less relevance to the subject for which the second concentration of the drug is being calculated.

The drug concentration prediction engine 815 can determine, using the full body circulation engine 300, the at least one drug characteristic, and the second concentration of the drug, a third concentration of a drug in a third blood flow entering a second organ. The third blood flow is downstream of the first organ. The second organ may be immediately downstream of the first organ, or may be separated from the first organ by one or more additional anatomical systems. For example, with reference to FIG. 3, the first organ may be the gut, and the second organ may be the liver, or the second organ may be the kidney. The third blood flow can be determined based on blood flow from a plurality of organs.

The drug concentration prediction engine 815 can initialize a second drug concentration model 820 (e.g., corresponding to the second organ) using the third concentration of the drug. The drug concentration engine 815 can determine, using the second drug concentration model 820, a fourth concentration of the drug in the second organ. The drug concentration engine 815 can output an indication of the fourth concentration of the drug in the second organ.

In some embodiments, the drug concentration prediction engine 815 modifies the second drug concentration model 820 using the at least one subject characteristic. The drug concentration prediction engine 815 can modify the second drug concentration model 820 prior to determining the fourth concentration of the drug. The drug concentration prediction engine 815 can modify the second drug concentration model 820 to make the second drug concentration model 820 more accurately predict the fourth concentration of the drug. The drug concentration prediction engine 815 can modify the second drug concentration model 820 by selecting the second drug concentration model 820 from among a plurality of pre-determined drug concentration models 820 based on the at least one subject characteristic. For example, if the at least one subject characteristic includes an age of the subject, the drug concentration prediction engine 815 can compare the age of the subject to an age (or age range) assigned to each of the plurality of pre-determined drug concentration models 820, and select the pre-determined drug concentration model 820 having an assigned age that matches the age of the at least one subject characteristic. The drug concentration prediction engine 815 can modify the second drug concentration model 820 by modifying a subject characteristic-dependent parameter of the second drug concentration model 820. For example, if the at least one subject characteristic includes the age of the subject, the drug concentration prediction engine 815 can modify an age-dependent parameter of the second drug concentration model 820 (e.g., if the second drug concentration model 820 is of the form $A=A_0*\exp(-k*t)$, where $A_0$ is the initial drug concentration, A is the drug concentration at time t, and k is an age-dependent parameter, the drug concentration prediction engine 815 can modify the value of the parameter k based on the age of the subject). The drug concentration prediction engine 815 can modify the subject-dependent parameter using a parameter mapping function (which may be trained based on subject data regarding a plurality of subjects, such as by using a regression model or other training operations described with reference to the DCPTS 400). By modifying the second drug concentration model 820 to be more specific to the subject based on the at least one subject characteristic, the drug concentration prediction engine 815 can more accurately determine the fourth concentration of the drug, such as by reducing dependence on over-generalized models that may have been constructed using subject data having relatively less relevance to the subject for which the fourth concentration of the drug is being calculated.

It will be appreciated that the drug concentrations determined by the drug concentration engine 815 may be drug concentrations at the same point in time. Unlike existing systems, which only estimate drug concentrations for a single organ, the concentration predictor 800 thus can provide a more accurate measure of drug concentrations throughout the body of the subject. For example, the concentration predictor 800 can use accurate representations of drug metabolism in upstream organs to determine drug concentration levels (and metabolism) in downstream organisms, reducing the need for inaccurate assumptions about feedback loops and other secondary effects regarding drug metabolism throughout the body.

Drug Concentration Prediction Display Engine

In some embodiments, the concentration predictor 800 includes a prediction display engine 850. The prediction display engine 850 is configured to generate a visualization of the output of the drug concentration engine 815. The prediction display engine 850 can provide a gamified visualization, enabling user inputs to be received to quickly modify various parameters and variables implemented by the concentration predictor 800 in generating drug concentration predictions. The prediction display engine 850 can output the visualization to the display device 130 for display by the display device 130.

In some embodiments, the prediction display engine 850 is executed by a graphics processing unit ("GPU") (not shown), which may be a dedicated GPU to improve the performance (e.g., reduce latency) of the visualization. The prediction display engine 850 can include a preconfigured visualization engine, such as an UNREAL gaming engine.

The prediction display engine 850 can generate the visualization to display drug concentrations at various points in time for various anatomical systems. In some embodiments, the visualization includes a user interface. The user input device 135 can receive user inputs corresponding to the user interface displayed with the visualization. For example, the user interface can include user interface elements corresponding to user inputs indicating commands such as to select a drug, select an organ or other anatomical system, select a dosage, select a point in time, or other commands associated with displaying and configuring display of drug concentration as a function of time. The prediction display engine 850 can generate the visualize to generate drug concentrations for a plurality of anatomical systems simultaneously, so that drug metabolism can be visualized in a manner not possible with existing systems.

Figure 10:
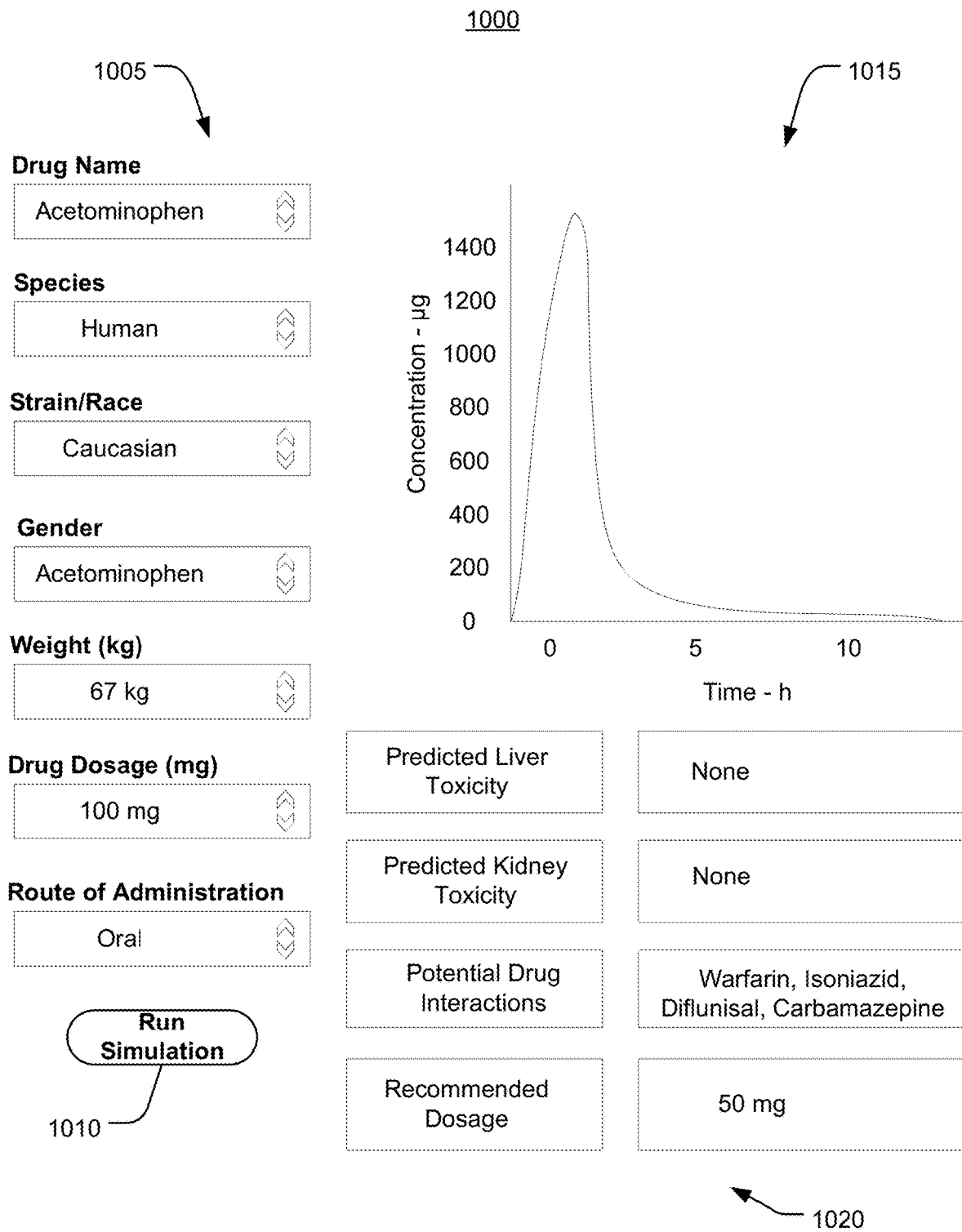
FIG. 10 is a schematic diagram of a visualization generated by a drug concentration prediction system, according to an embodiment of the present disclosure.

For example, referring briefly to FIG. 10, the prediction display engine 850 can generate a visualization 1000. The visualization 1000 includes a plurality of user input fields 1005, which can receive information such as subject characteristics and drug information. For example, the visualization 1000 is illustrated to include user input fields 1005 for drug name, subject species, subject strain/race, subject gender, subject weight, drug dosage, and route of administration. Responsive to receiving input via a run simulation field 1010, the prediction display engine 850 can cause the concentration predictor 800 to calculate drug concentration and other information using the information received via the plurality of user input fields 1005. The prediction display engine 850 can use information generated by the concentration predictor 800 to generate a drug concentration chart 1015 illustrating predicted drug concentration as a function of time, and also to generate drug metabolism information 1020, such as predicted toxicity for particular organs, potential drug interactions, and recommended dosages (e.g., based on information generated by toxicity calculator 860, dosage recommendation engine 870, and/or drug recommendation engine 880 as described below).

Toxicity Calculator

In some embodiments, the concentration predictor 800 includes a toxicity calculator 860. The toxicity calculator 860 can compare a drug concentration level generated by the concentration predictor 800 to a corresponding toxicity threshold to generate a toxicity recommendation. The toxicity threshold may be specific to a selected organ. The drug concentration level used for the comparison may be a peak drug concentration level. The drug concentration level may be an indication of AUC. The drug concentration level may be a variety of other representations of drug concentration, such as half life, or concentration after a predetermined amount of time.

In some embodiments, the toxicity calculator 860 compares the drug concentration level to the corresponding toxicity, and outputs an indication of whether the drug concentration level exceeds the corresponding toxicity. The toxicity calculator 860 can compare the drug concentration level in a first organ to a corresponding first toxicity, compare the drug concentration level in a second organ to a corresponding second toxicity, and output an indication of whether at least one of the first toxicity or the second toxicity has been exceeded. The toxicity calculator 860 can calculate the toxicities based on a disease condition (e.g., disease stage) or other subject characteristic, such as by making the toxicities relatively lower as severity of a disease increases.

In some embodiments, the concentration predictor 800 receives the indication of whether the at least one toxicity has been exceeded, and modifies the drug dosage (e.g., drug dosage 325) to reduce the drug concentration levels in the first and/or second organs until the corresponding toxicity thresholds are not exceeded.

Dosage Recommendation Engine

In some embodiments, the concentration predictor 800 includes a dosage recommendation engine 870. The dosage recommendation engine 870 can generate a recommended dosage based on information from the subject database 805 and the toxicity recommendation generated by the toxicity calculator 860. For example, the dosage recommendation engine 870 can identify target drug dosage values (or ranges of values) based on information regarding the subject such as age, sex, weight, genetic conditions, dosage history, or subject-specific toxicity information. The dosage recommendation engine 870 can receive the indication of whether toxicity threshold(s) have been exceeded from the toxicity calculator 860, and modify the dosage to be less than a threshold dosage at which toxicity is exceeded.

Drug Recommendation Engine

The concentration predictor 800 can include a drug recommendation engine 880. The drug recommendation engine 880 can generate a recommendation to administer the drug to the subject. The drug recommendation engine 880 can compare drug concentration levels, toxicity recommendations, and dosage recommendations for a plurality of candidate drugs, and recommend one or more of the candidate drugs based on the comparison. The drug recommendation engine 880 can retrieve information regarding the subject from the subject database 805, such as known interactions (or allergies) between the subject and the candidate drugs, to determine whether to recommend certain candidate drugs. The drug recommendation engine 880 can recommend the candidate drug(s) based on a disease condition of the subject. The drug recommendation engine 880 can recommend a delivery method (e.g., oral vs. intravenous) based on calculated drug concentrations, such as to more effectively target desired anatomical systems while avoiding anatomical systems where drug concentrations reach or exceed toxicity thresholds.

The drug recommendation engine 880 can execute at least one policy, heuristic, or other set of rules to recommend the one or more candidate drugs. In some embodiments, the rules may include: recommending drugs which do not cause allergies or other unwanted interactions; recommending drugs which have an AUC which is at least one of less than a maximum AUC or greater than a minimum AUC; recommending drugs which have a maximum concentration ($C_{max}$) which is at least one of less than a maximum $C_{max}$ or greater than a minimum $C_{max}$; recommending drugs which have relatively higher efficacy; recommending drugs which have relatively higher efficacy for a known characteristic of the subject, such as age, weight, sex, race/ethnicity, or genetic condition; recommending drugs which have similar structure to other drugs for which more information is available regarding efficacy.

Figure 9:
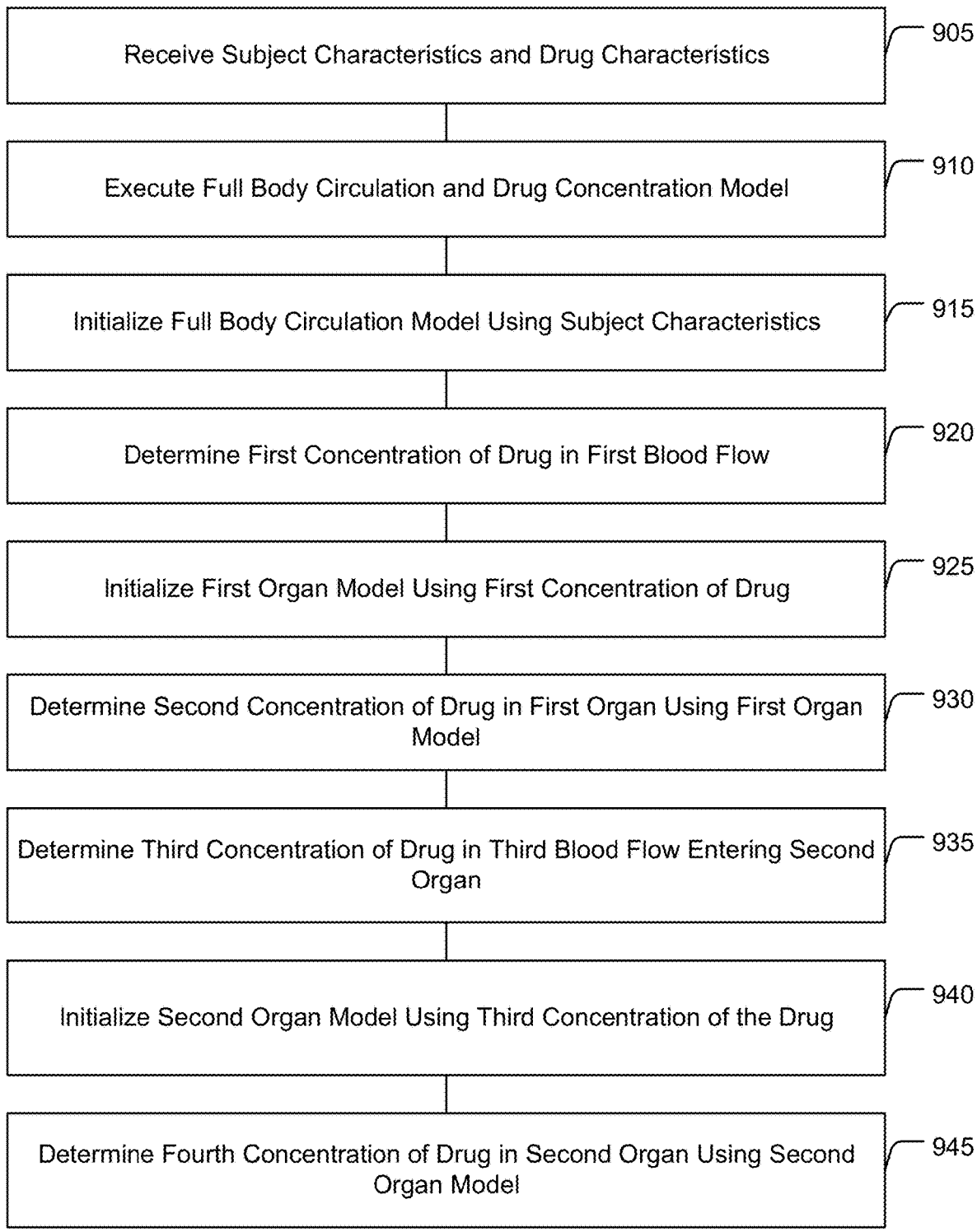
FIG. 9 is a flow diagram of a method for predicting drug concentration levels as a function of time in one or more organs of a subject, according to an embodiment of the present disclosure.

Referring now to FIG. 9, a method 900 for predicting drug concentration levels as a function of time in one or more organs of a subject is shown according to an embodiment of the present disclosure. The method 900 can be executed using various systems described herein, such as the full body circulation engine 300, DCPTS 400, and concentration predictor 800.

At 905, at least one subject characteristic of the subject and at least one drug characteristic of a drug to be administered to the subject are received. The at least one subject characteristic can be similar to the at least one subject characteristic of the training database 405, including but not limited to age, sex, and weight. The at least one drug characteristic can be similar to the parameters of the drug parameter database 430, including but not limited to drug structure, solubility, fraction unbound, lipophilicity, effective molecular weight, and pKa.

At 910, a full body circulation and drug concentration model is executed. Executing the full body circulation and drug concentration model includes initializing, at 915, a full body circulation model using the at least one subject characteristic. Blood flow rates in the circulatory system of the subject and between various anatomical systems of the subject can be determined using the full body circulation model.

Executing the full body circulation and drug concentration model includes determining, at 920, using the full body circulation model and the at least one drug characteristic, a first concentration of the drug in a first blood flow entering a first organ. The first concentration may be determined based on an indication of a drug dosage of the drug to be administered to the subject. The drug concentration may be determined at a selected point in time.

Executing the full body circulation and drug concentration model includes initializing, at 925, a first organ model corresponding to the first organ using the first concentration of the drug, and determining, at 930, using the first organ model, a second concentration of the drug in the first organ. The second concentration of the drug may be an indication of drug concentration at a selected point in time. In some embodiments, the first drug concentration model is modified using the at least one subject characteristic. The first drug concentration model can be modified prior to determining the second concentration of the drug. The first drug concentration model can be modified to make the first drug concentration model more accurately predict the second concentration of the drug. The first drug concentration model can be modified by selecting the first drug concentration model from among a plurality of pre-determined drug concentration models based on the at least one subject characteristic. For example, if the at least one subject characteristic includes an age of the subject, the age of the subject can be compared to an age (or age range) assigned to each of the plurality of pre-determined drug concentration models, and the pre-determined drug concentration model having an assigned age that matches the age of the at least one subject characteristic can be selected. The first drug concentration model can be modified by modifying a subject characteristic-dependent parameter of the first drug concentration model. For example, if the at least one subject characteristic includes the age of the subject, an age-dependent parameter of the first drug concentration model can be modified (e.g., if the first drug concentration model is of the form $A=A_0*\exp(-k*t)$, where $A_0$ is the initial drug concentration, A is the drug concentration at time t, and k is an age-dependent parameter, the value of the parameter k can be modified based on the age of the subject). The subject-dependent parameter can be modified using a parameter mapping function (which may be trained based on subject data regarding a plurality of subjects, such as by using a regression model or other training operations described with reference to the DCPTS 400). By modifying the first drug concentration model to be more specific to the subject based on the at least one subject characteristic, the second concentration of the drug can be more accurately determined, such as by reducing dependence on over-generalized models that may have been constructed using subject data having relatively less relevance to the subject for which the second concentration of the drug is being calculated.

Executing the full body circulation and drug concentration model includes determining, at 935, using the full body circulation model, the at least one drug characteristic, and the second concentration of the drug, a third concentration of the drug in a third blood flow entering a second organ, the third blood flow downstream of the first organ. The third blood flow is downstream of the first organ. The second organ may be immediately downstream of the first organ, or may be separated from the first organ by one or more additional anatomical systems. For example, with reference to FIG. 3, the first organ may be the gut, and the second organ may be the liver, or the second organ may be the kidney.

Executing the full body circulation and drug concentration model includes initializing, at 940, a second drug concentration model corresponding to the second organ using the third concentration of the drug, and determining, at 945, using the second drug concentration model model, a fourth concentration of the drug in the second organ. In some embodiments, the drug concentrations can be displayed simultaneously (e.g., representing drug concentrations in different organs at the same point in time). In some embodiments, the second drug concentration model is modified using the at least one subject characteristic. The second drug concentration model can be modified prior to determining the fourth concentration of the drug. The second drug concentration model can be modified to make the second drug concentration model more accurately predict the fourth concentration of the drug. The second drug concentration model can be modified by selecting the second drug concentration model from among a plurality of pre-determined drug concentration models based on the at least one subject characteristic. For example, if the at least one subject characteristic includes an age of the subject, the age of the subject can be compared to an age (or age range) assigned to each of the plurality of pre-determined drug concentration models, and the pre-determined drug concentration model having an assigned age that matches the age of the at least one subject characteristic can be selected. The second drug concentration model can be modified by modifying a subject characteristic-dependent parameter of the second drug concentration model. For example, if the at least one subject characteristic includes the age of the subject, an age-dependent parameter of the second drug concentration model can be modified (e.g., if the first drug concentration model is of the form $A=A_0*\exp(-k*t)$, where $A_0$ is the initial drug concentration, A is the drug concentration at time t, and k is an age-dependent parameter, the value of the parameter k can be modified based on the age of the subject). The subject-dependent parameter can be modified using a parameter mapping function (which may be trained based on subject data regarding a plurality of subjects, such as by using a regression model or other training operations described with reference to the DCPTS 400). By modifying the second drug concentration model to be more specific to the subject based on the at least one subject characteristic, the fourth concentration of the drug can be more accurately determined, such as by reducing dependence on over-generalized models that may have been constructed using subject data having relatively less relevance to the subject for which the fourth concentration of the drug is being calculated.

The construction and arrangement of the systems and methods as shown in the various exemplary embodiments are illustrative only. Although only a few embodiments have been described in detail in this disclosure, many modifications are possible (e.g., variations in sizes, dimensions, structures, and proportions of the various elements, values of parameters, etc.). For example, the position of elements may be reversed or otherwise varied and the nature or number of discrete elements or positions may be altered or varied. Accordingly, all such modifications are intended to be included within the scope of the present disclosure. The order or sequence of any process or method steps may be varied or re-sequenced according to alternative embodiments. Other substitutions, modifications, changes, and omissions may be made in the design, operating conditions and arrangement of the exemplary embodiments without departing from the scope of the present disclosure.

Although the figures show a specific order of method steps, the order of the steps may differ from what is depicted. Also two or more steps may be performed concurrently or with partial concurrence. Such variation will depend on the software and hardware systems chosen and on designer choice. All such variations are within the scope of the disclosure. Likewise, software implementations could be accomplished with standard programming techniques with rule based logic and other logic to accomplish the various connection steps, processing steps, comparison steps and decision steps.

What is claimed is:

1. A system for predicting drug concentration levels as a function of time in one or more organs of a subject, comprising:
   a subject database including a plurality of characteristics of the subject;
   a drug database including at least one characteristic of a drug to be administered to the subject; and
   one or more processors configured to:

train a first drug concentration prediction model of a first organ by performing machine learning by iteratively performing the following steps until a first comparison result is minimized or is less than a first threshold difference:
  providing, to the first drug concentration prediction model, as input, a plurality of first subject profiles, each first subject profile corresponding to a respective first training subject, each first subject profile comprising i) an identifier of the drug, ii) a plurality of first known concentration-time pairs, each first known concentration-time pair comprising a first known concentration of the drug in the first organ at a first known time, and iii) a characteristic of the first training subject,
  outputting, by executing the first drug concentration prediction model, a plurality of first predicted concentration-time pairs, each first predicted concentration-time pair comprising a first predicted concentration of the drug at the first known time of a corresponding first known concentration-time pair,
  comparing each first predicted concentration of the drug to a respective first known concentration of the drug to generate the first comparison result; and
  adjusting at least one parameter of the first drug concentration prediction model based on the first comparison result;
train a second drug concentration prediction model of a second organ by performing machine learning by iteratively performing the following steps until a second comparison result is minimized or is less than a second threshold difference:
  providing, to the second drug concentration prediction model, as input, a plurality of second subject profiles, each second subject profile corresponding to a respective second training subject, each second subject profile comprising i) an identifier of the drug, ii) a plurality of second known concentration-time pairs, each second known concentration-time pair comprising a second known concentration of the drug at a second known time, and iii) a characteristic of the second training subject,
  outputting, by executing the second drug concentration prediction model, a plurality of second predicted concentration-time pairs, each second predicted concentration-time pair comprising a second predicted concentration of the drug at the second known time of a corresponding second known concentration-time pair;
  comparing each second predicted concentration of the drug to a respective second known concentration of the drug to generate the second comparison result, and
  adjusting at least one parameter of the second drug concentration prediction model based on the second comparison result;
determine, using a first subset of the plurality of characteristics of the subject, a first blood flow rate to the first organ and a second blood flow rate to the second organ of the subject;
determine a first concentration of the drug in a first blood flow entering the first organ based on an initial drug dosage and the first blood flow rate to the first organ;
modify, using a second subset of the plurality of characteristics of the subject, the trained first drug concentration prediction model of the first organ;
determine a second concentration of the drug in the first organ using the modified first drug concentration prediction model;
determine a third concentration of the drug in a second blood flow entering the second organ downstream of the first organ based on the second concentration and the second blood flow rate to the second organ;
modify, using a third subset of the plurality of characteristics of the subject, the trained second drug concentration prediction model of the second organ;
determine a fourth concentration of the drug in the second organ using the modified second drug concentration prediction model;
provide, as output, an indication of a recommendation for administering the drug for the subject responsive to comparing:
  (i) the second concentration of the drug in the first organ to a first maximum concentration for the first organ;
  ii) a first area under curve (AUC) based on first concentration levels of the drug within a first time duration in the first organ to a first maximum AUC for the first organ;
  (iii) the fourth concentration of the drug in the second organ to a second maximum concentration for the second organ; and
  iv) a second AUC based on second concentration levels of the drug within a second time duration in the second organ to a second maximum AUC for the second organ.

2. The system of claim 1, wherein the one or more processors are configured to generate a visualization of the second concentration of the drug in the first organ and the fourth concentration of the drug in the second organ, and cause a display device to display the visualization.

3. The system of claim 1, wherein the one or more processors are configured to determine the first maximum concentration based on a disease condition of the subject.

4. The system of claim 1, wherein the one or more processors are configured to generate a dosage recommendation for the subject based on the subject database and at least one of the second concentration of the drug or the fourth concentration of the drug.

5. The system of claim 1, wherein the one or more processors are configured to compare an efficacy of the drug to a threshold efficacy, and generate a recommendation to administer the drug to the subject based on the subject database and whether the efficacy exceeds the threshold efficacy.

6. The system of claim 1, wherein the at least one characteristic of the plurality of characteristics of the subject includes at least one of an age, sex, height, weight, disease condition, secondary condition, or genetic condition of the subject.

7. The system of claim 1, wherein the at least one characteristic of the drug includes at least one of a solubility, a fraction unbound, a lipophilicity, an effective molecular weight, or a pKa of the drug.

8. A method, comprising:
  training, by one or more processors, a first drug concentration prediction model of a first organ by performing machine learning by iteratively performing the following steps until a first comparison result is minimized or is less than a first threshold difference:

providing, as input to the first drug concentration prediction model, a plurality of first subject profiles, each first subject profile corresponding to a respective first training subject, each first subject profile comprising i) an identifier of a drug, ii) a plurality of first known concentration-time pairs, each first known concentration-time pair comprising a first known concentration of the drug at a first known time, and iii) a characteristic of the first training subject, outputting, by executing the first drug concentration prediction model, a plurality of first predicted concentration-time pairs, each first predicted concentration-time pair comprising a first predicted concentration of the drug at the first known time of a corresponding first known concentration-time pair, comparing each first predicted concentration of the drug to a respective first known concentration of the drug to generate the first comparison result; and adjusting at least one parameter of the first drug concentration prediction model responsive to the first comparison result;

training, by the one or more processors, a second drug concentration prediction model of a second organ by performing machine learning by iteratively performing the following steps until a second comparison result is minimized or is less than a second threshold difference:

providing, as input to the second drug concentration prediction model, a plurality of second subject profiles, each second subject profile corresponding to a respective second training subject, each second subject profile comprising i) an identifier of the drug, ii) a plurality of second known concentration-time pairs, each second known concentration-time pair comprising a second known concentration of the drug at a second known time, and iii) a characteristic of the second training subject, outputting, by executing the second drug concentration prediction model, a plurality of second predicted concentration-time pairs, each second predicted concentration-time pair comprising a second predicted concentration of the drug at the second known time of a corresponding second known concentration-time pair, comparing each second predicted concentration of the drug to a respective second known concentration of the drug to generate the second comparison result; and adjusting at least one parameter of the second drug concentration prediction model responsive to the second comparison result;

determining, by the one or more processors using a first subset of a plurality of characteristics of a subject, a first blood flow rate of a first blood flow to the first organ and a second blood flow rate of a second blood flow to the second organ;

determining, by the one or more processors, a first concentration of the drug in the first blood flow;

modifying, by the one or more processors using a second subset of the plurality of characteristics of the subject, the trained first drug concentration prediction model;

determining, by the one or more processors, a second concentration of the drug in the first organ using the modified first drug concentration prediction model and the first concentration of the drug;

determining, by the one or more processors, a third concentration of the drug in a second blood flow entering the second organ downstream of the first organ based on the second concentration and the second blood flow rate to the second organ;

modifying, by the one or more processors using a third subset of the plurality of characteristics of the subject, the trained second drug concentration prediction model;

determining, by the one or more processors, a fourth concentration of the drug in the second organ using the modified second drug concentration prediction model and the third concentration of the drug; and outputting an indication of a recommendation for administering the drug for the subject responsive to comparing:

(i) the second concentration of the drug in the first organ to a first maximum concentration for the first organ;

ii) a first area under curve (AUC) based on first concentration levels of the drug within a first time duration in the first organ to a first maximum AUC for the first organ;

(iii) the fourth concentration of the drug in the second organ to a second maximum concentration for the second organ; and iv) a second AUC based on second concentration levels of the drug within a second time duration in the second organ to a second maximum AUC for the second organ.

9. The method of claim 8, further comprising outputting a first value at a first point in time of the second concentration of the drug, and outputting a second value at the first point in time of the fourth concentration of the drug.

10. The method of claim 8, further comprising generating a visualization of the second concentration of the drug in the first organ and the fourth concentration of the drug in the second organ, and causing a display device to display the visualization.

11. The method of claim 8, further comprising determining the first maximum concentration based on a disease condition of the subject.

12. The method of claim 8, further comprising comparing an efficacy of the drug to a threshold efficacy, and generating a recommendation to administer the drug to the subject based on the subject database and whether the efficacy exceeds the threshold efficacy.

13. The method of claim 8, wherein at least one characteristic of the subject includes at least one of an age, sex, height, weight, disease condition, secondary condition, or genetic condition of the subject.

14. The method of claim 8, wherein at least one characteristic of the drug includes at least one of a solubility, a fraction unbound, a lipophilicity, an effective molecular weight, or a pKa of the drug.

15. The method of claim 8, further comprising generating a dosage recommendation for the subject based on the subject database and at least one of the second concentration of the drug or the fourth concentration of the drug and administering the drug to the subject using the dosage recommendation.

16. The method of claim 8, further comprising generating the recommendation to include a delivery modality for the drug of oral delivery or intravenous delivery based on the second concentration of the drug and the fourth concentration of the drug.

* * * * *